United States Patent
Kwong et al.

(10) Patent No.: US 9,386,657 B2
(45) Date of Patent: Jul. 5, 2016

(54) ORGANIC ELECTROLUMINESCENT MATERIALS AND DEVICES

(75) Inventors: Raymond Kwong, Fo Tan (HK); Sze Kui Lam, Kowloon (HK); Alexey Dyatkin, Ambler, PA (US)

(73) Assignee: Universal Display Corporation, Ewing, NJ (US)

( * ) Notice: Subject to any disclaimer, the term of this patent is extended or adjusted under 35 U.S.C. 154(b) by 1086 days.

(21) Appl. No.: 13/421,430

(22) Filed: Mar. 15, 2012

(65) Prior Publication Data

US 2013/0241400 A1 Sep. 19, 2013

(51) Int. Cl.
| | |
|---|---|
| H01L 51/50 | (2006.01) |
| H05B 33/10 | (2006.01) |
| C07D 405/14 | (2006.01) |
| C07D 409/14 | (2006.01) |
| C07D 421/14 | (2006.01) |
| C09K 11/06 | (2006.01) |
| C07D 209/86 | (2006.01) |
| C07D 209/88 | (2006.01) |
| H01L 51/00 | (2006.01) |

(52) U.S. Cl.
CPC .............. *H05B 33/10* (2013.01); *C07D 209/86* (2013.01); *C07D 209/88* (2013.01); *C07D 405/14* (2013.01); *C07D 409/14* (2013.01); *C07D 421/14* (2013.01); *C09K 11/06* (2013.01); *H01L 51/0054* (2013.01); *H01L 51/0072* (2013.01); *H01L 51/0073* (2013.01); *H01L 51/0074* (2013.01); *C09K 2211/1007* (2013.01); *C09K 2211/1011* (2013.01); *C09K 2211/1029* (2013.01); *C09K 2211/1088* (2013.01); *C09K 2211/1092* (2013.01); *C09K 2211/1096* (2013.01); *H01L 51/0085* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Baldo et al., "Highly Efficient Phosphorescent Emission from Organic Electroluminescent Devices," Nature, vol. 395, 151-154, (1998).

(Continued)

*Primary Examiner* — Gregory Clark
(74) *Attorney, Agent, or Firm* — Duane Morris LLP

(57) ABSTRACT

Novel tricarbazole compounds are provided. By appropriately selecting the nature of the tricarbazole substituents, compounds with appropriate HOMO and LUMO energies can be obtained for use as materials in a secondary hole transport layer.

24 Claims, 3 Drawing Sheets

(56) References Cited

U.S. PATENT DOCUMENTS

| | | | |
|---|---|---|---|
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 7,968,146 B2 | 6/2011 | Wagner et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0105202 A1* | 5/2006 | Kitamura | 428/690 |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2012/0181524 A1* | 7/2012 | Kato et al. | 257/40 |
| 2013/0105787 A1* | 5/2013 | Tanaka | C07D 209/86 257/40 |

FOREIGN PATENT DOCUMENTS

| | | | | |
|---|---|---|---|---|
| EP | 2034538 | 3/2009 | | |
| JP | 199507352 | 1/1996 | | |
| JP | 200511610 | 1/2005 | | |
| JP | 2007123392 | 5/2007 | | |
| JP | 2007254297 | 10/2007 | | |
| JP | 2008074939 | 10/2009 | | |
| KR | 2009028943 | * 3/2009 | | C09K 11/06 |
| KR | 20090028943 | 3/2009 | | |
| WO | WO 0139234 | 5/2001 | | |
| WO | WO 0202714 | 1/2002 | | |
| WO | WO 0215645 | 2/2002 | | |
| WO | WO 03040257 | 5/2003 | | |
| WO | WO 03060956 | 7/2003 | | |
| WO | WO 2004093207 | 10/2004 | | |
| WO | WO 2004107822 | 12/2004 | | |
| WO | WO 2005014551 | 2/2005 | | |
| WO | WO 2005019373 | 3/2005 | | |
| WO | WO 2005030900 | 4/2005 | | |
| WO | WO 2005089025 | 9/2005 | | |
| WO | WO 2005123873 | 12/2005 | | |
| WO | WO 2006009024 | 1/2006 | | |
| WO | WO 2006056418 | 6/2006 | | |
| WO | WO 2006072002 | 7/2006 | | |
| WO | WO 2006082742 | 8/2006 | | |
| WO | WO 2006098120 | 9/2006 | | |
| WO | WO 2006100298 | 9/2006 | | |
| WO | WO 2006103874 | 10/2006 | | |
| WO | WO 2006114966 | 11/2006 | | |
| WO | WO 2006132173 | 12/2006 | | |
| WO | WO 2007002683 | 1/2007 | | |
| WO | WO 2007004380 | 1/2007 | | |
| WO | WO 2007063754 | 6/2007 | | |
| WO | WO 2007063796 | 6/2007 | | |
| WO | WO 2008056746 | 5/2008 | | |
| WO | WO 2008057394 | 5/2008 | | |
| WO | WO 2008101842 | 8/2008 | | |
| WO | WO 2008132085 | 11/2008 | | |
| WO | WO 2009000673 | 12/2008 | | |
| WO | WO 2009003898 | 1/2009 | | |
| WO | WO 2009008311 | 1/2009 | | |
| WO | WO 2009018009 | 2/2009 | | |
| WO | WO 2009050290 | 4/2009 | | |
| WO | WO 2009021126 | 5/2009 | | |
| WO | WO 2009062578 | 5/2009 | | |
| WO | WO 2009063833 | 5/2009 | | |
| WO | WO 2009066778 | 5/2009 | | |
| WO | WO 2009066779 | 5/2009 | | |
| WO | WO 2009086028 | 7/2009 | | |
| WO | WO 2009100991 | 8/2009 | | |
| WO | WO 2010011390 | 1/2010 | | |
| WO | WO 2010050778 | 5/2010 | | |

OTHER PUBLICATIONS

Baldo et al., "Very high-efficiency green organic light-emitting devices based on electrophosphorescence," Appl. Phys. Lett., vol. 75, No. 3, 4-6 (1999).

Brunner et al, "Carbazole Compounds as Host Materials for Triplet Emitters in Organic Light-Emitting Diodes: Tuning the HOMO Level without Influencing the Triplet Energy in Small Molecules" J. Am. Chem. Soc. 2004, 126, 6035-6042.

Feng et al., "Synthesis and Optical Properties of Starburst Carbazoles Based on 9-Phenylcarbazole Core" SYNLETT 2006, No. 17, pp. 2841-2845.

Hyun et al., "Synthesis and electroluminescent properties of para- and meta-tolyl carbazyl derivatives" Thin Solid Films 209 (2006) 127-131.

Kim et al., "Molecular Crystals and Liquid Crystals. Synthesis and Hole-Transporting Properties of Phenyl-Carbazyl Derivatives" Princeton University, Nov. 6, 2011, Publisher: Taylor & Francis.

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

(56) References Cited

OTHER PUBLICATIONS

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).
Tung, Yung-Liang et al., "Organic Light-Emitting Diodes Based on Charge-Neutral Ru$^{II}$ PHosphorescent Emitters," *Adv. Mater.*, 17(8):1059-1064 (2005).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).
Wong, Wai-Yeung, "Multifunctional Iridium Complexes Based on Carbazole Modules as Highly Efficient Electrophosphors," *Angew. Chem. Int. Ed.*, 45:7800-7803 (2006).
Tang, C.W. and VanSlyke, S.A., "Organic Electroluminescent Diodes," *Appl. Phys. Lett.*, 51(12):913-915 (1987).
Adachi, Chihaya et al., "Organic Electroluminescent Device Having a Hole Conductor as an Emitting Layer," *Appl. Phys. Lett.*, 55(15):1489-1491 (1989).
Ma, Yuguang et al., "Triplet Luminescent Dinuclear-Gold(I) Complex-Based Light-Emitting Diodes with Low Turn-On voltage," *Appl. Phys. Lett.*, 74(10):1361-1363 (1999).
Gao, Zhiqiang et al., "Bright-Blue Electroluminescence From a Silyl-Substituted ter-(phenylene-vinylene) derivative," *Appl. Phys. Lett.*, 74(6):865-867 (1999).
Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).
Hung, L.S. et al., "Anode Modification in Organic Light-Emitting Diodes by Low-Frequency Plasma Polymerization of CHF$_3$," *Appl. Phys. Lett.*, 78(5):673-675 (2001).
Ikai, Masamichi and Tokito, Shizuo, "Highly Efficient Phosphorescence From Organic Light-Emitting Devices with an Exciton-Block Layer," *Appl. Phys. Lett.*, 79(2):156-158 (2001).
Wang, Y. et al., "Highly Efficient Electroluminescent Materials Based on Fluorinated Organometallic Iridium Compounds," *Appl. Phys. Lett.*, 79(4):449-451 (2001).
Kwong, Raymond C. et al., "High Operational Stability of Electrophosphorescent Devices," *Appl. Phys. Lett.*, 81(1):162-164 (2002).
Holmes, R.J. et al., "Blue Organic Electrophosphorescence Using Exothermic Host-Guest Energy Transfer," *Appl. Phys. Lett.*, 82(15):2422-2424 (2003).
Sotoyama, Wataru et al., "Efficient Organic Light-Emitting Diodes with Phosphorescent Platinum Complexes Containing N^C^N-Coordinating Tridentate Ligand," *Appl. Phys. Lett.*, 86:153505-1-153505-3 (2005).
Okumoto, Kenji et al., "Green Fluorescent Organic Light-Emitting Device with External Quantum Efficiency of Nearly 10%," *Appl. Phys. Lett.*, 89:063504-1-063504-3 (2006).
Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).
Aonuma, Masaki et al., "Material Design of Hole Transport Materials Capable of Thick-Film Formation in Organic Light Emitting Diodes," *Appl. Phys. Lett.*, 90:183503-1-183503-3 (2007).
Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).
Adachi, Chihaya et al., "High-Efficiency Red Electrophosphorescence Devices," *Appl. Phys. Lett.*, 78(11):1622-1624 (2001).
Wong, Keith Man-Chung et al., A Novel Class of Phosphorescent Gold(III) Alkynyl-Based Organic Light-Emitting Devices with Tunable Colour, *Chem. Commun.*, 2906-2908 (2005).
Hamada, Yuji et al., "High Luminance in Organic Electroluminescent Devices with Bis(10-hydroxybenzo[h]quinolinato)beryllium as an Emitter," *Chem. Lett.*, 905-906 (1993).
Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).
Mi, Bao-Xiu et al., "Thermally Stable Hole-Transporting Material for Organic Light-Emitting Diode: an Isoindole Derivative," *Chem. Mater.*, 15(16):3148-3151 (2003).
Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).
Niu, Yu-Hua et al., "Highly Efficient Electrophosphorescent Devices with Saturated Red Emission from a Neutral Osmium Complex," *Chem. Mater.*, 17(13):3532-3536 (2005).
Lo, Shih-Chun et al., "Blue Phosphorescence from Iridium(III) Complexes at Room Temperature," *Chem. Mater.*, 18(21):5119-5129 (2006).
Takizawa, Shin-ya et al., "Phosphorescent Iridium Complexes Based on 2-Phenylimidazo[1,2- α]pyridine Ligands: Tuning of Emission Color toward the Blue Region and Application to Polymer Light-Emitting Devices," *Inorg. Chem.*, 46(10):4308-4319 (2007).
Lamansky, Sergey et al., "Synthesis and Characterization of Phosphorescent Cyclometalated Iridium Complexes," *Inorg. Chem.*, 40(7):1704-1711 (2001).
Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).
Noda, Tetsuya and Shirota, Yasuhiko, "5,5'-Bis(dimesitylboryl)-2,2'-bithiophene and 5,5'-Bis(dimesitylboryl)-2,2':5',2"-terthiophene as a Novel Family of Electron-Transporting Amorphous Molecular Materials," *J. Am. Chem. Soc.*, 120 (37):9714-9715 (1998).
Sakamoto, Youichi et al., "Synthesis, Characterization, and Electron-Transport Property of Perfluorinated Phenylene Dendrimers," *J. Am. Chem. Soc.*, 122(8):1832-1833 (2000).
Adachi, Chihaya et al., "Nearly 100% Internal Phosphorescence Efficiency in an Organic Light Emitting Device," *J. Appl. Phys.*, 90(10):5048-5051 (2001).
Shirota, Yasuhiko et al., "Starburst Molecules Based on π-Electron Systems as Materials for Organic Electroluminescent Devices," *Journal of Luminescence*, 72-74:985-991 (1997).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).
Kido, Junji et al., 1,2,4-Triazole Derivative as an Electron Transport Layer in Organic Electroluminescent Devices, *Jpn. J. Appl. Phys.*, 32:L917-L920 (1993).
Van Slyke, S. A. et al., "Organic Electroluminescent Devices with Improved Stability," *Appl. Phys. Lett.*, 69(15):2160-2162 (1996).
Guo, Tzung-Fang et al., "Highly Efficient Electrophosphorescent Polymer Light-Emitting Devices," *Organic Electronics*, 1:15-20 (2000).
Palilis, Leonidas C., "High Efficiency Molecular Organic Light-Emitting Diodes Based on Silole Derivatives and Their Exciplexes," *Organic Electronics*, 4:113-121 (2003).
Ikeda, Hisao et al., "P-185: Low-Drive-Voltage OLEDs with a Buffer Layer Having Molybdenum Oxide," *SID Symposium Digest*, 37:923-926 (2006).
T. Östergård et al., "Langmuir-Blodgett Light-Emitting Diodes of Poly(3-Hexylthiophene): Electro-Optical Characteristics Related to Structure," *Synthetic Metals*, 87:171-177 (1997).
Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).
Salbeck, J. et al., "Low Molecular Organic Glasses for Blue Electroluminescence," *Synthetic Metals*, 91:209-215 (1997).

* cited by examiner

Formula I

ORGANIC ELECTROLUMINESCENT MATERIALS AND DEVICES

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel tricarbazole compounds. In particular, these compounds are useful as materials that can be incorporated into a secondary hole transport layer in OLED devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

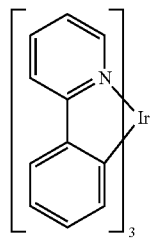

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

In one aspect, a compound having the formula:

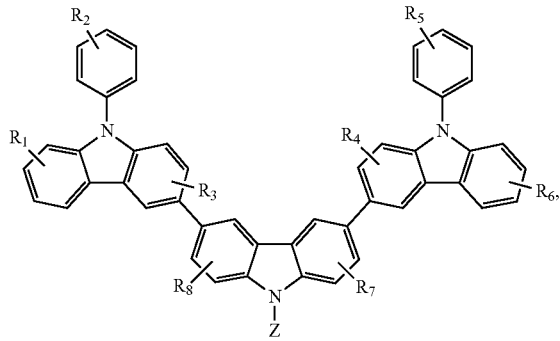

Formula I is provided. In the compound of Formula I, Z is selected from the group consisting of:

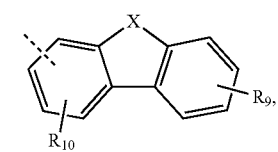

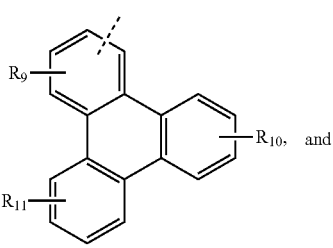

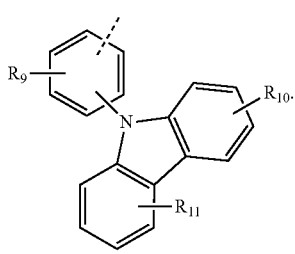

X is selected from the group consisting of NR, O, S, and Se, $R_1$ to $R_{11}$ independently represent mono, di, tri, tetra substitution, or no substitution, and R and $R_1$ and $R_{11}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $R_1$ to $R_{11}$ represent no substitution. In one aspect, $R_1$ to $R_{11}$ are independently aryl or heteroaryl.

In one aspect, the compound has the formula:

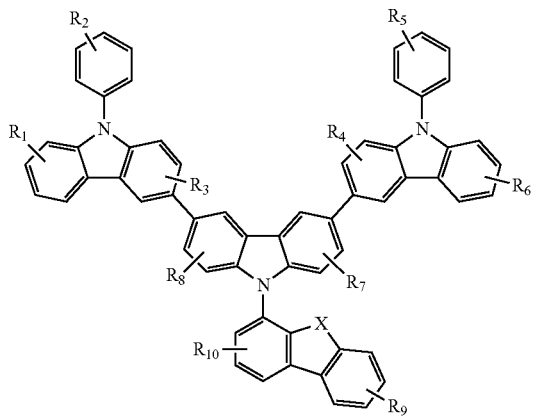

or

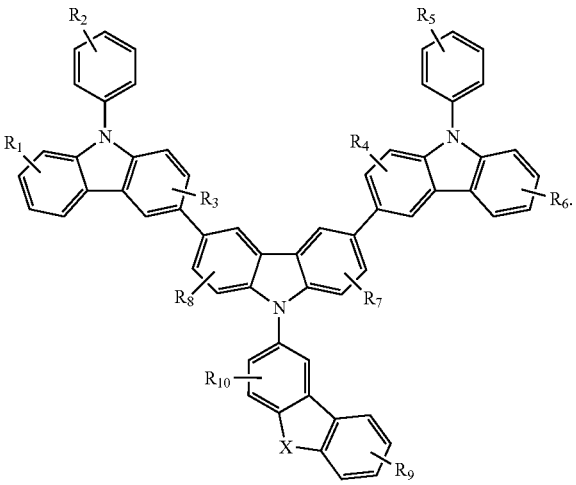

In one aspect, the compound has the formula:

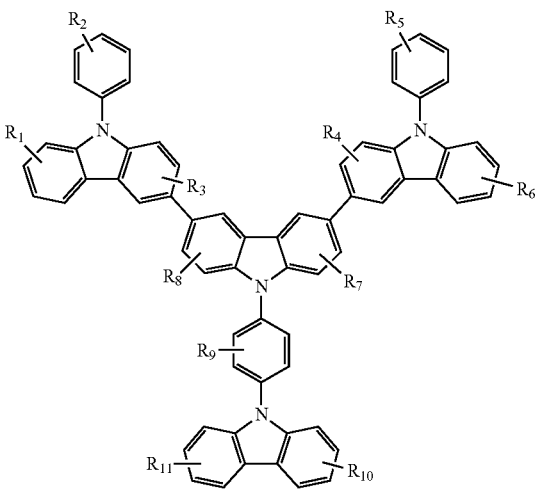

or

-continued
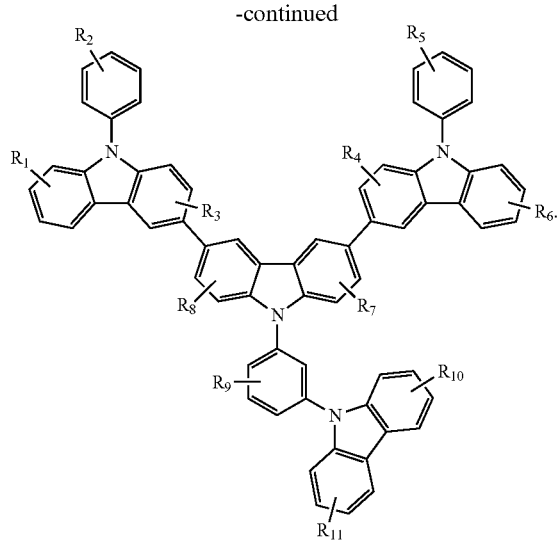
In one aspect, the compound has the formula:
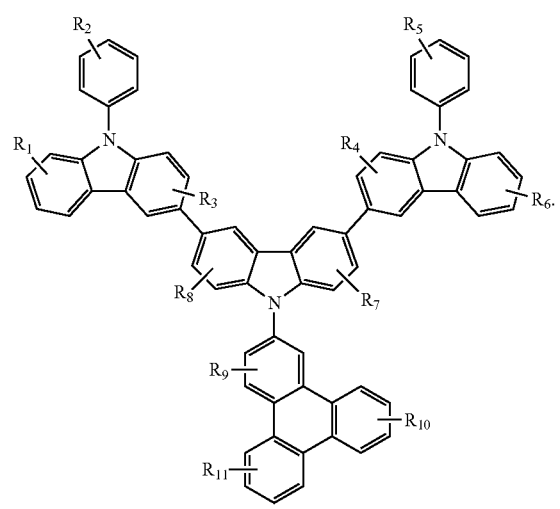
In one aspect, X is O or S. In one aspect, $R_2$ and $R_5$ represent no substitution. In one aspect, R is selected from the group consisting of alkyl, heteroalkyl, aralkyl, aryl and heteroaryl.
In one aspect, the compound is selected from the group consisting of:
Compound 5
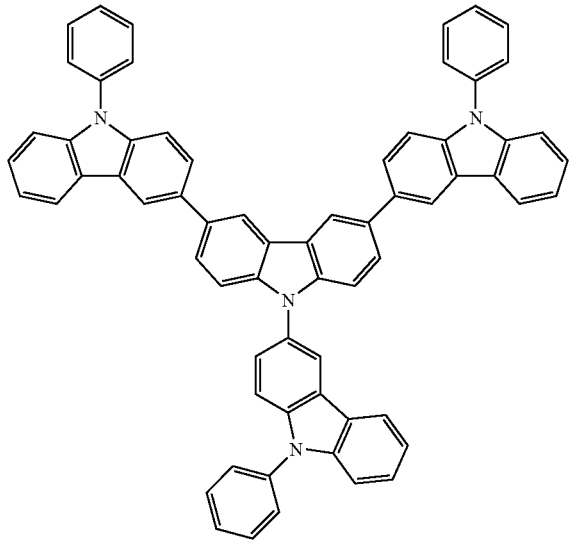
,
Compound 6
Compound 7
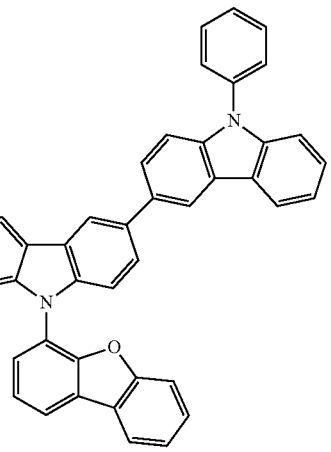
, Compound 8
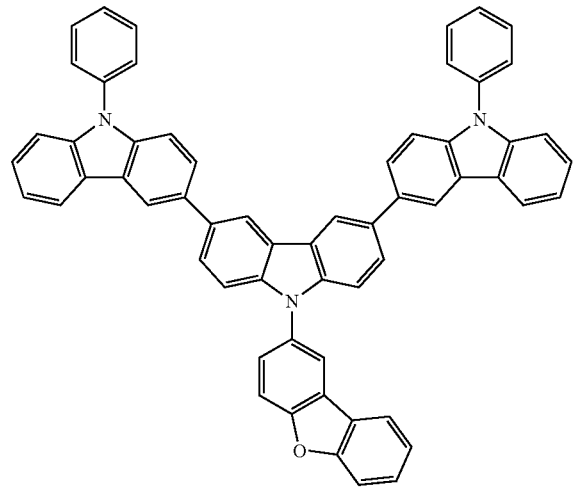
Compound 11
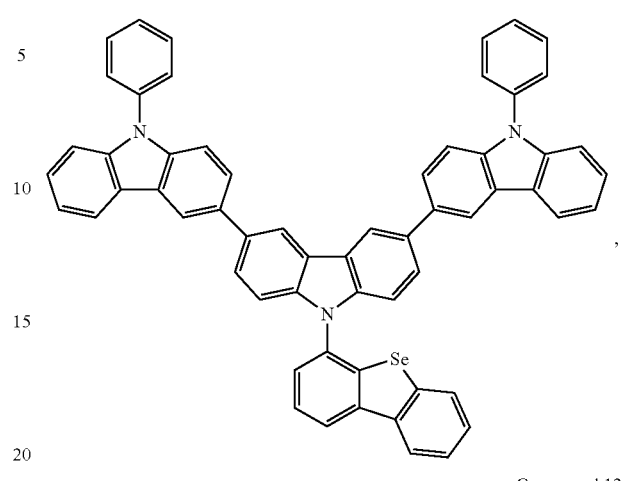
Compound 9
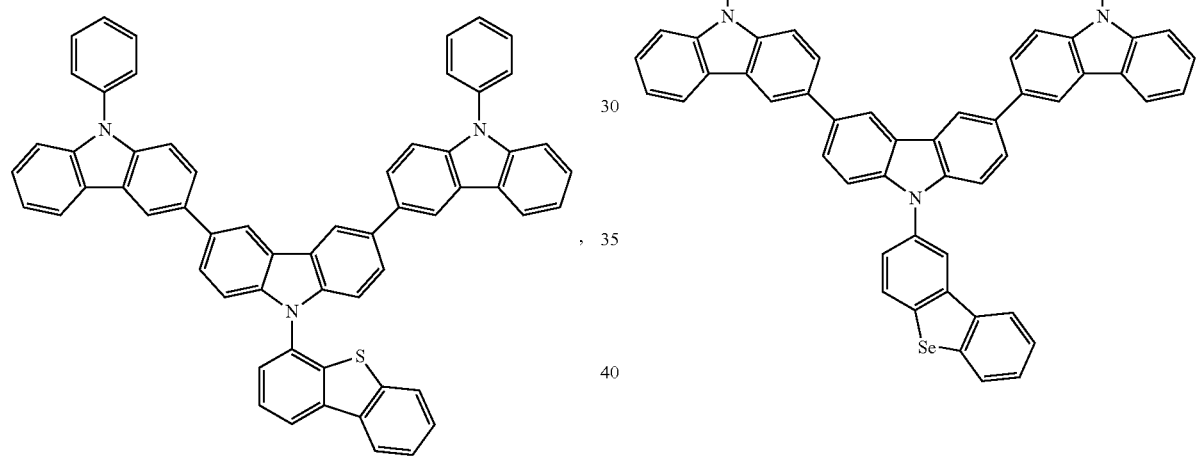
Compound 12
Compound 10
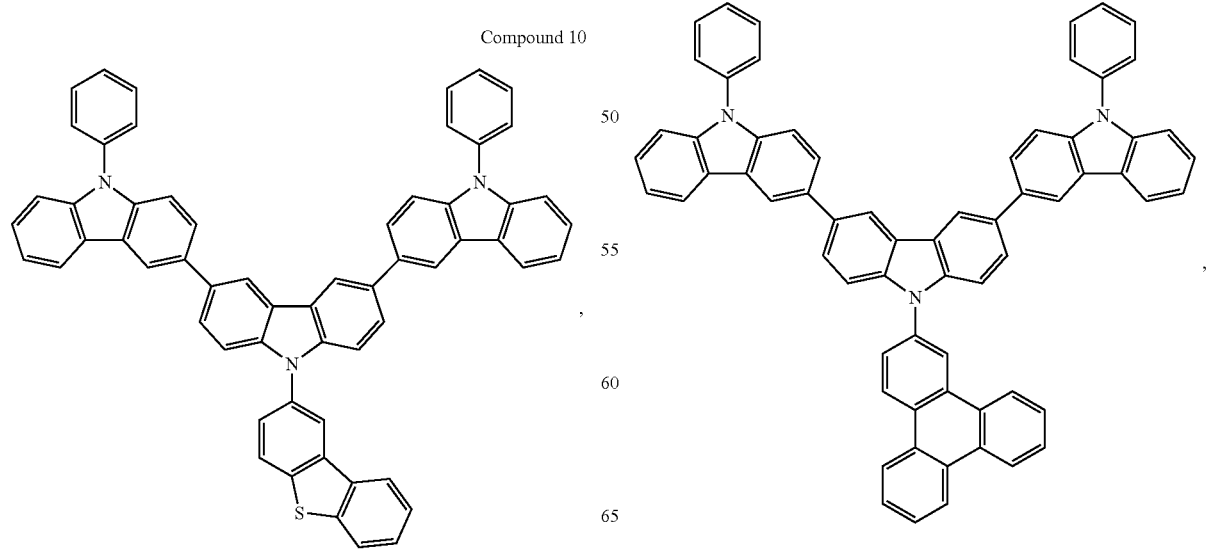
Compound 13

Compound 14

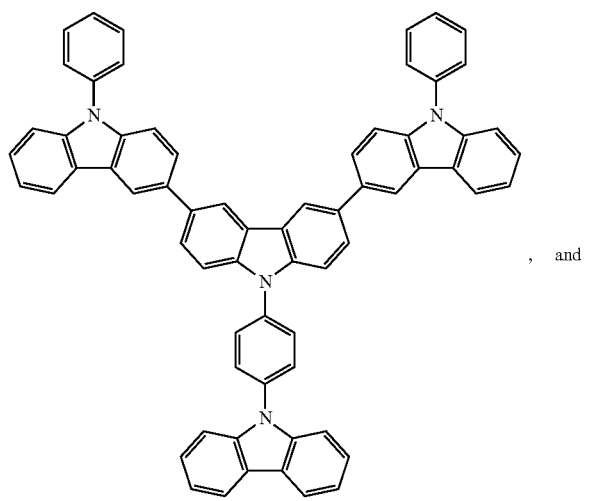

, and

Compound 15

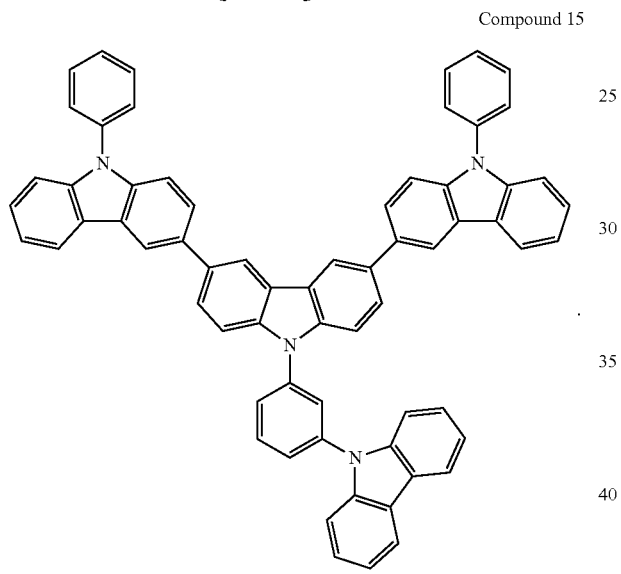

In one aspect, a first device is provided. The first device comprises a first organic light emitting device, further comprising: an anode, a cathode, a hole injection layer disposed between the anode and the emissive layer, a first hole transport layer disposed between the hole injection layer and the emissive layer, and a second hole transport layer disposed between the first hole transport layer and the emissive layer, wherein the second hole transport layer comprises a compound of formula:

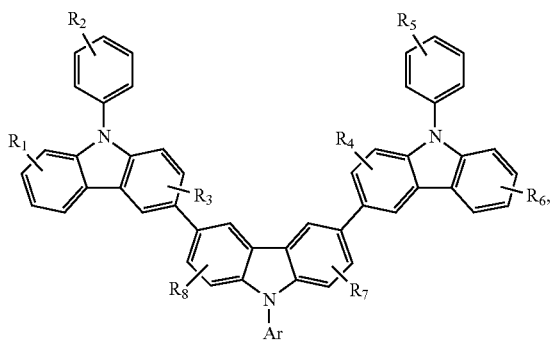

Formula II. In the compound of Formula II, Ar comprises aryl or heteroaryl, $R_1$ to $R_8$ independently represent mono, di, tri, tetra substitution, or no substitution, and $R_1$ to $R_8$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the second hole transport layer is disposed adjacent to the first hole transport layer. In one aspect, the first hole transport layer is thicker than the second hole transport layer.

In one aspect, Ar is selected from the group consisting of:

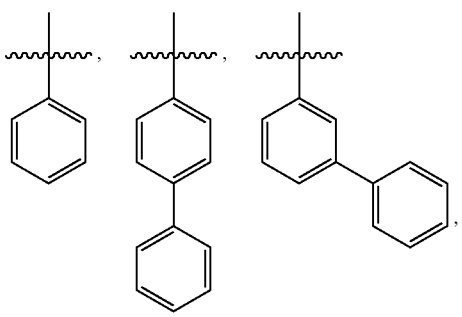

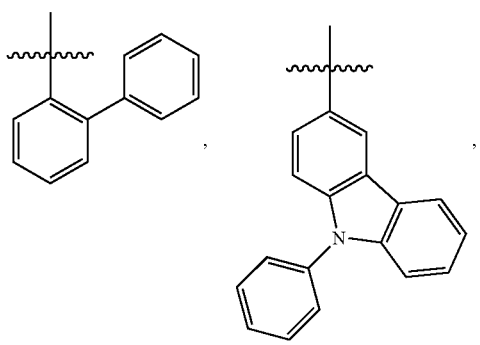

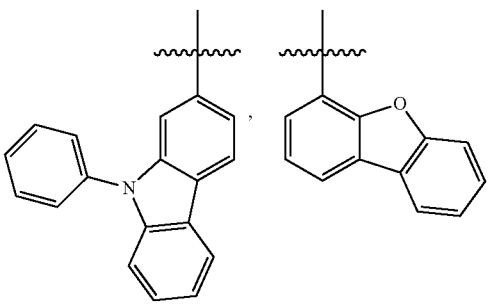

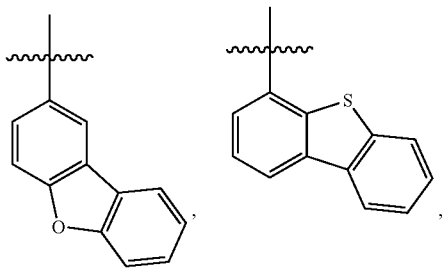

-continued

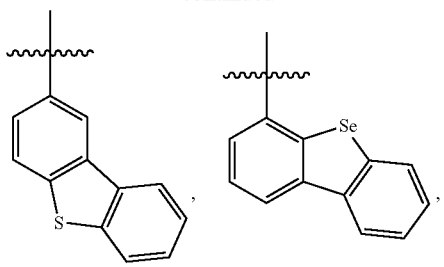

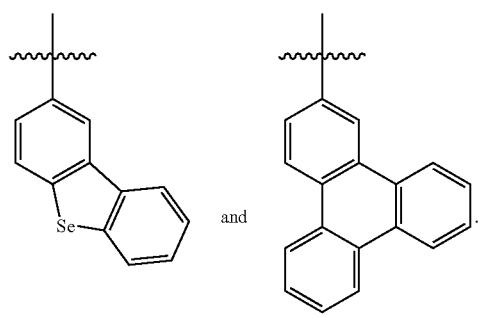 [SMILES: *c1ccc2[se]c3ccccc3c2c1 ; *c1ccc2c3ccccc3c3ccccc3c2c1]

In one aspect, the compound has the formula:

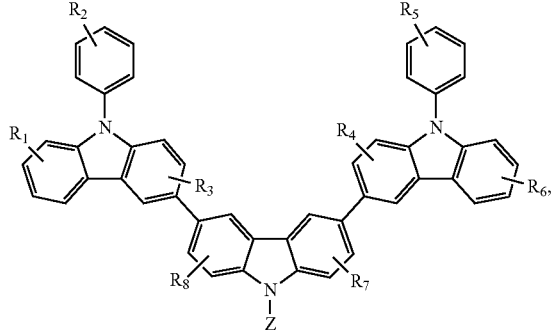

Formula I. In the compound of Formula I, Z is selected from the group consisting of:

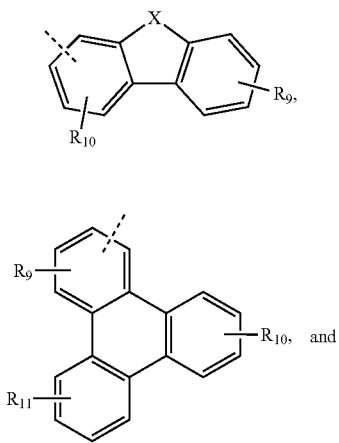

-continued

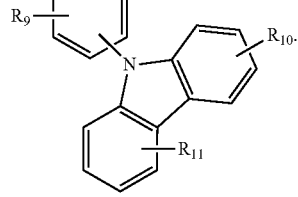

X is selected from the group consisting of NR, O, S, and Se, $R_9$, $R_{10}$, and $R_{11}$ independently represent mono, di, tri, tetra substitution, or no substitution, and R, $R_9$, $R_{10}$, and $R_{11}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the first hole transport layer comprises a compound with the formula:

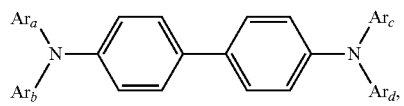

wherein $Ar_a$, $Ar_b$, $Ar_c$ and $Ar_d$ are independently selected from the group consisting of aryl and heteroaryl.

In one aspect, the triplet energy of the compound of Formula II is higher than the emission energy of the emissive layer.

In one aspect, the first device further comprises an emissive dopant comprising a transition metal complex having at least one ligand or part of the ligand if the ligand is more than bidentate selected from the group consisting of:

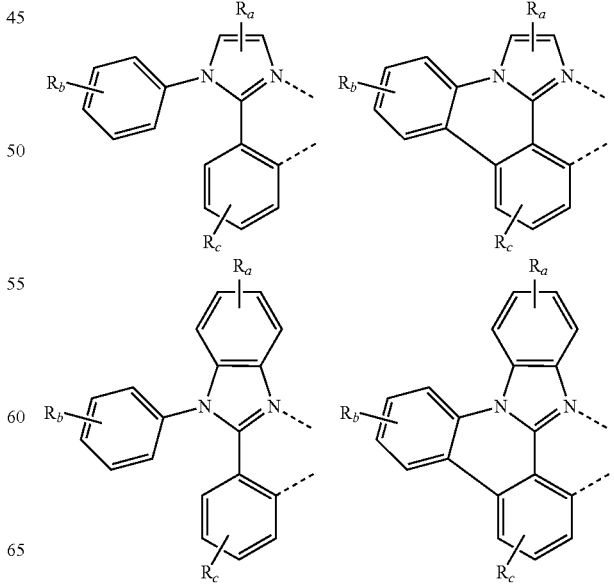

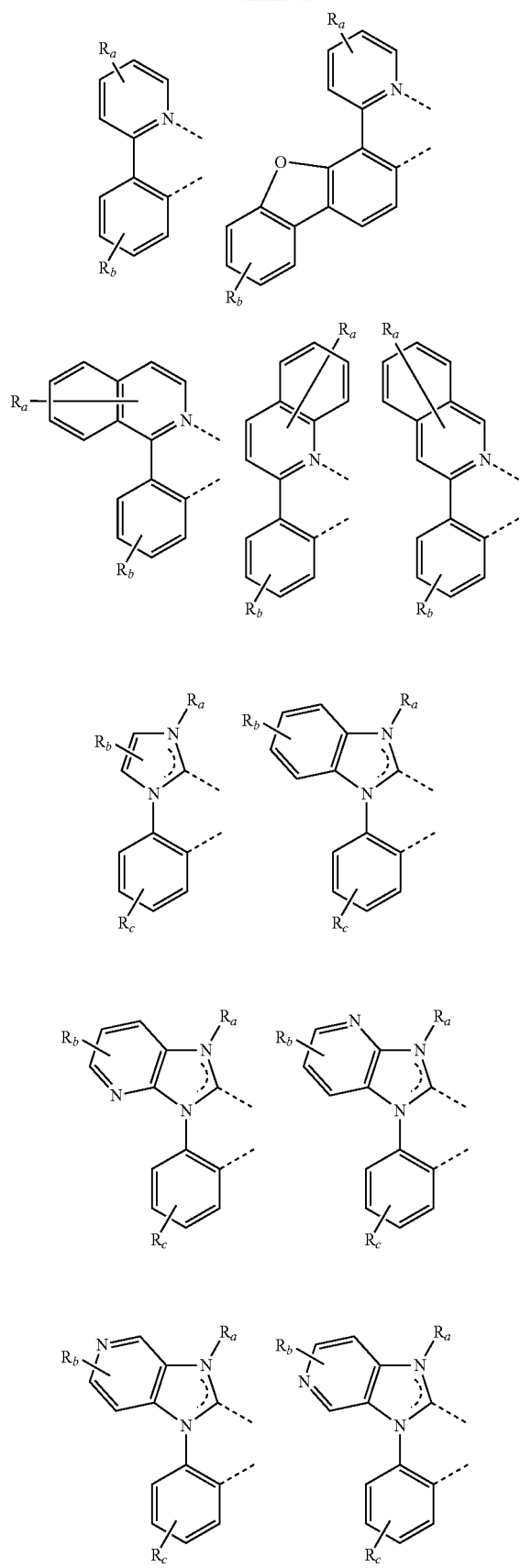

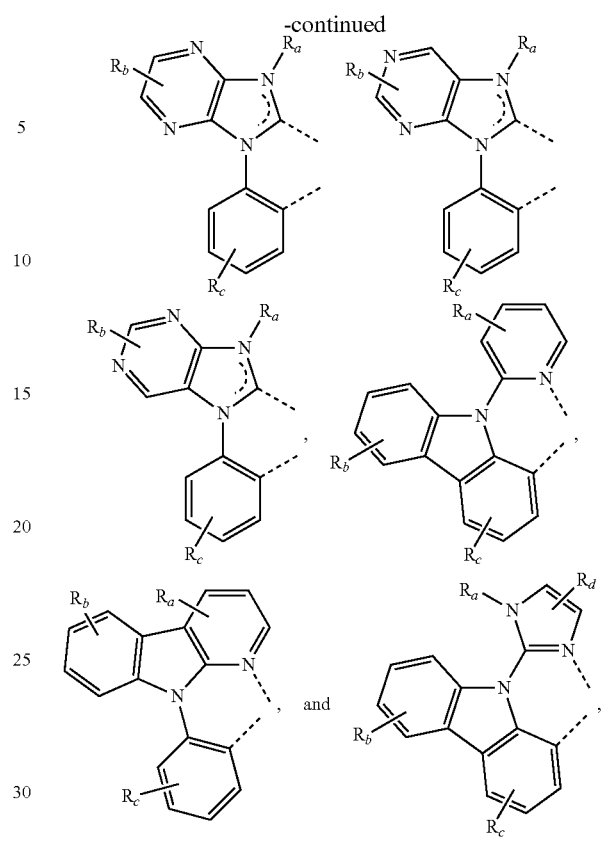

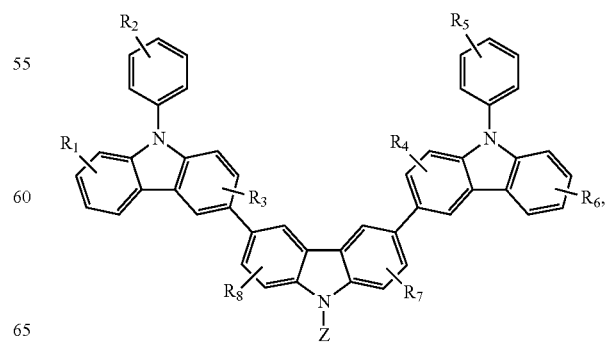

wherein $R_a$, $R_b$, $R_c$, and $R_d$ may represent mono, di, tri, or tetra substitution, or no substitution, wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof; and wherein two adjacent substituents of $R_a$, $R_b$, $R_c$, and $R_d$ are optionally joined to form a fused ring or form a multidentate ligand.

In one aspect, the first device is a consumer product. In one aspect, the first device is an organic light-emitting device. In one aspect, the first device comprises a lighting panel.

In one aspect, a first device comprising an organic light emitting device, further comprising: an anode, a cathode, a first organic layer disposed between the anode and the cathode; and wherein the first organic layer comprises a compound of formula:

Formula I. In the compound of Formula I, Z is selected from the group consisting of:

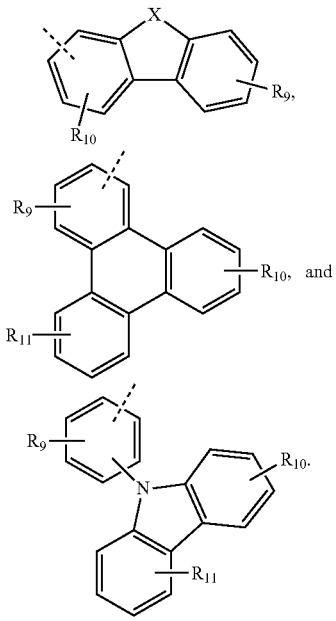

X is selected from the group consisting of NR, O, S, and Se, $R_1$ to $R_{11}$ independently represent mono, di, tri, tetra substitution, or no substitution; and R, and $R_1$ to $R_{11}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the first organic layer is an emissive layer. In one aspect, the emissive layer is a phosphorescent emissive layer.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
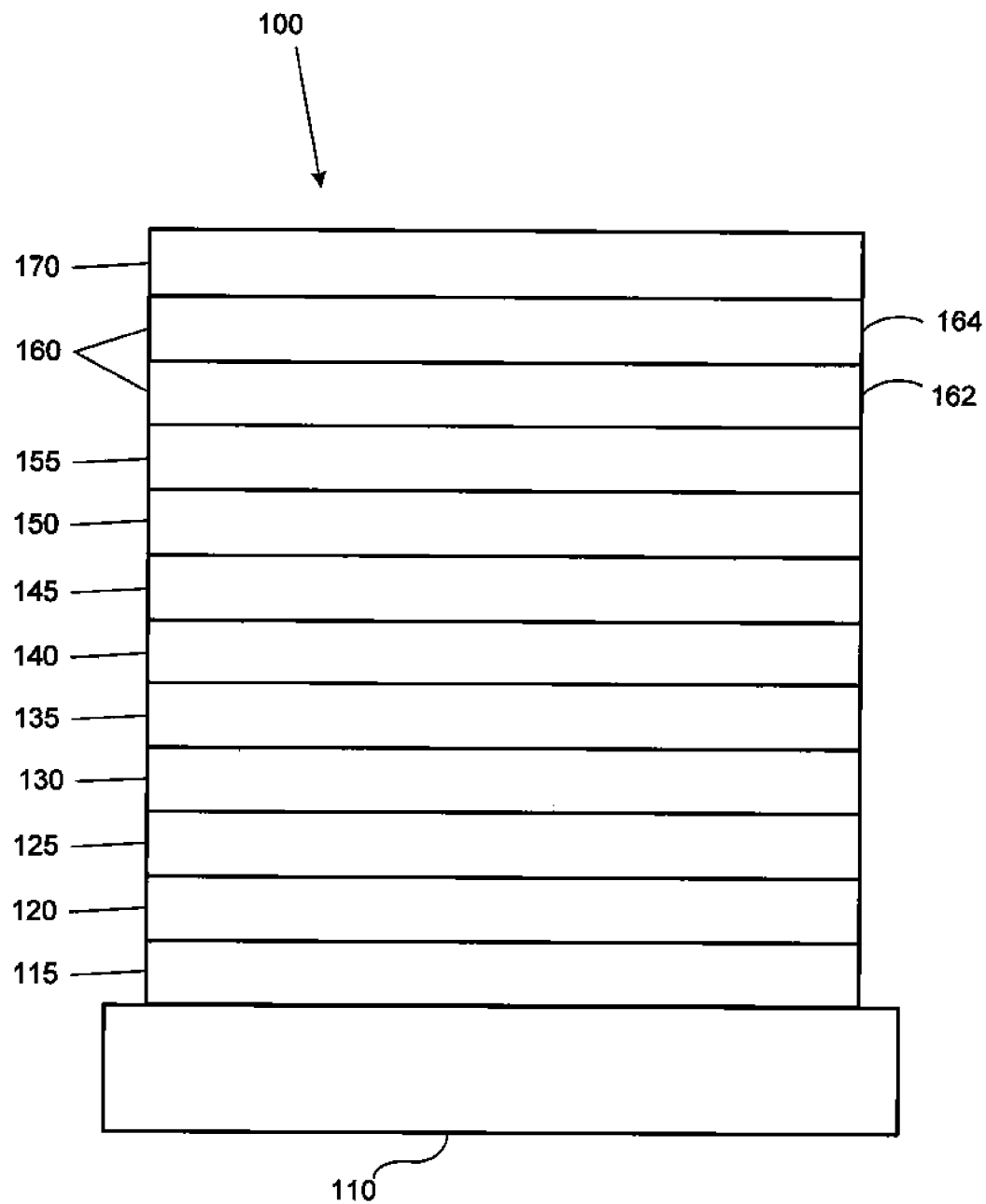
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
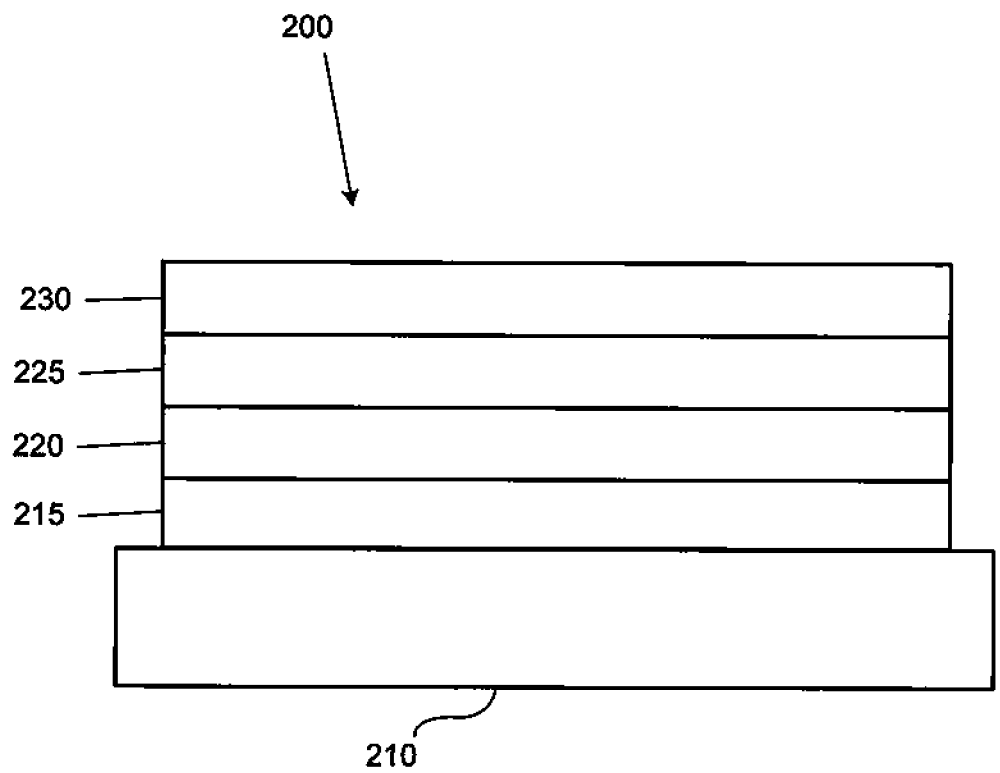
FIG. 2 shows an inverted organic light emitting device that does not have a separate electron transport layer.
Figure 3:
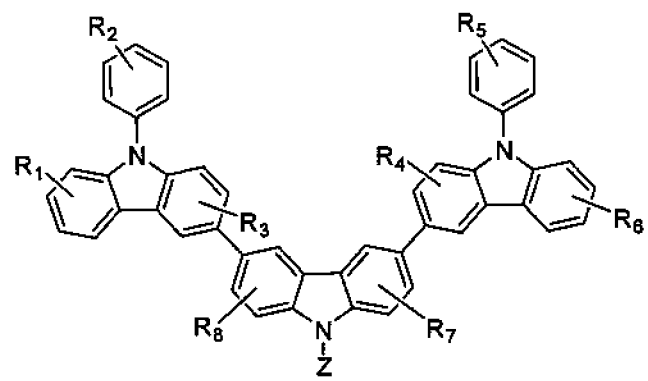
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

In one embodiment, a compound having the formula:

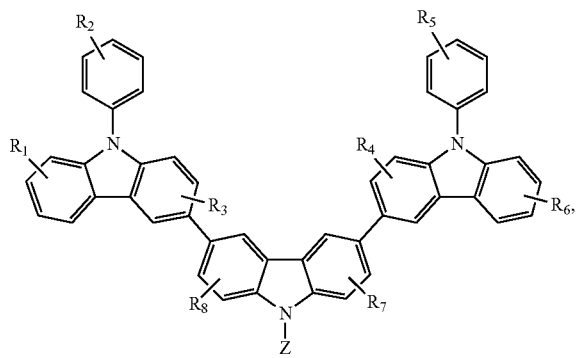

Formula I is provided. In the compound of Formula I, Z is selected from the group consisting of:

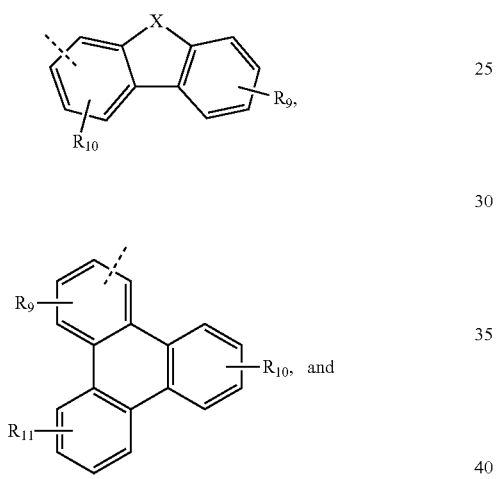

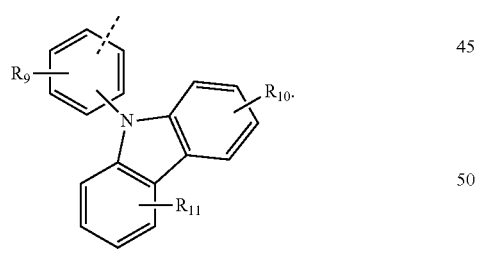

X is selected from the group consisting of NR, O, S, and Se, $R_1$ to $R_{11}$ independently represent mono, di, tri, tetra substitution, or no substitution, and R and $R_1$ to $R_{11}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, $R_1$ to $R_{11}$ represent no substitution. In one embodiment, $R_1$ to $R_{11}$ are independently aryl or heteroaryl.

In one embodiment, the compound has the formula:

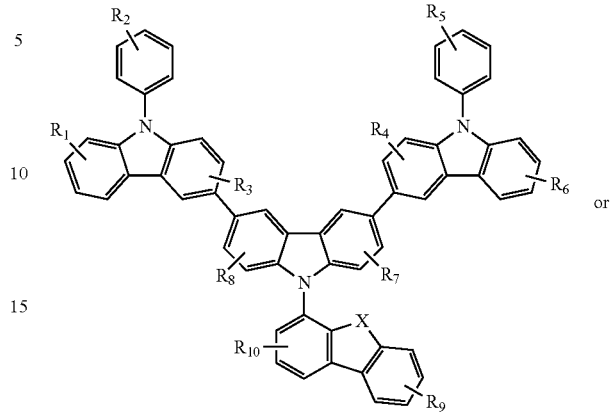

or

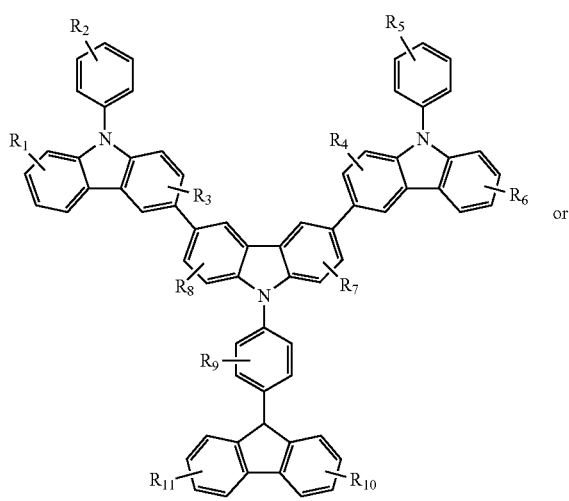

In one embodiment, the compound has the formula:

or

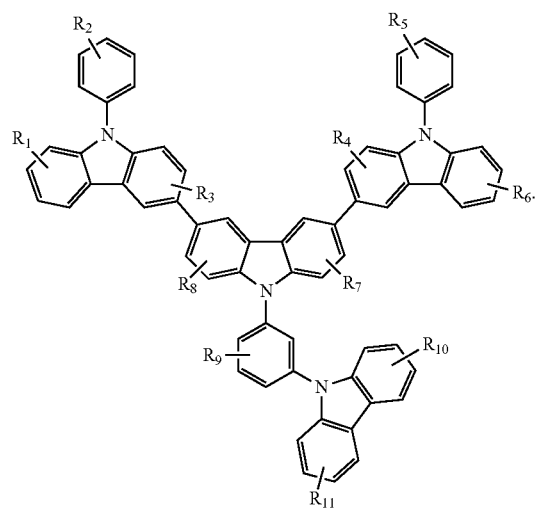
In one embodiment, the compound has the formula:
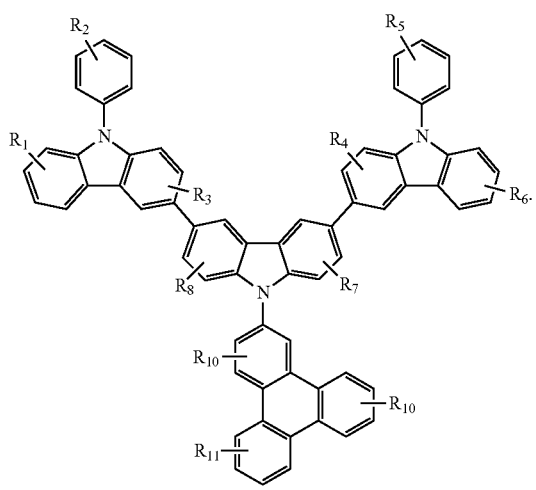
In one embodiment, X is O or S. In one embodiment, $R_2$ and $R_5$ represent no substitution. In one embodiment, R is selected from the group consisting of alkyl, heteroalkyl, aralkyl, aryl and heteroaryl.
In one embodiment, the compound is selected from the group consisting of:
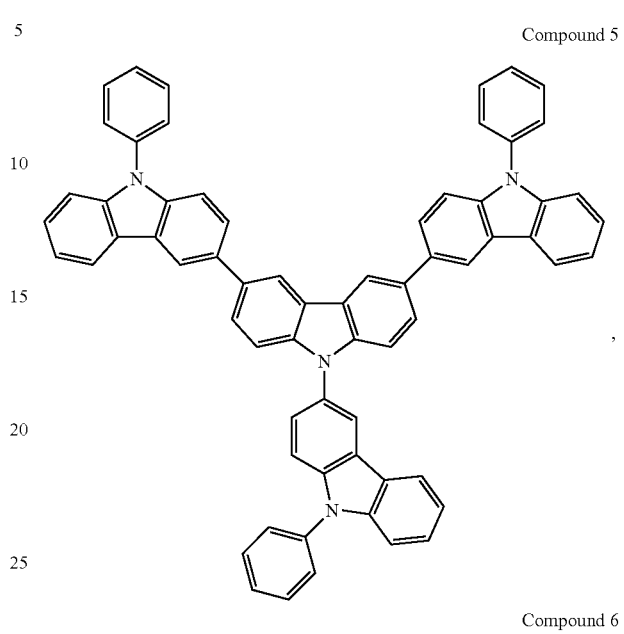
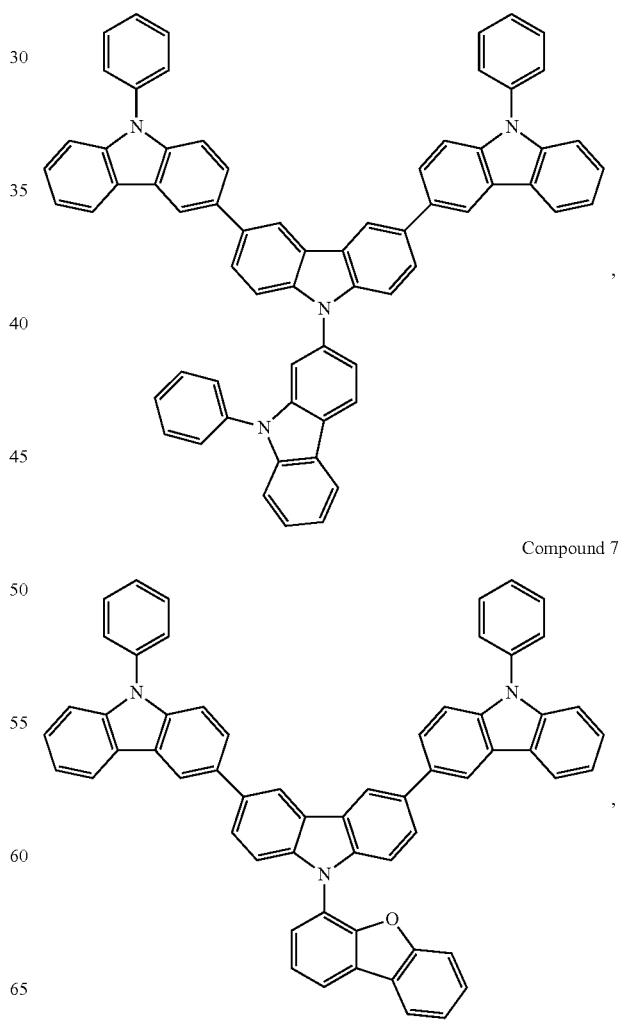

Compound 8
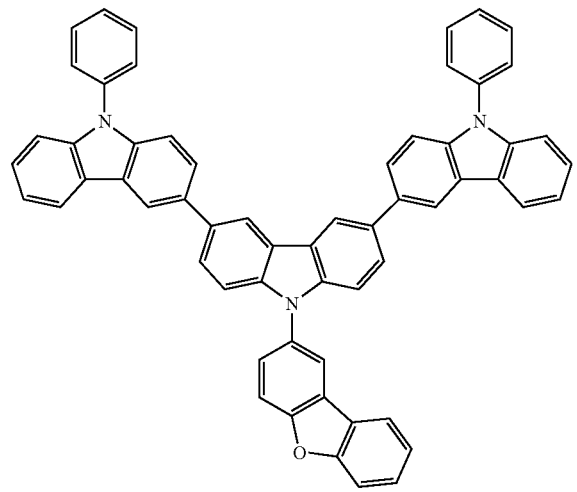
Compound 9
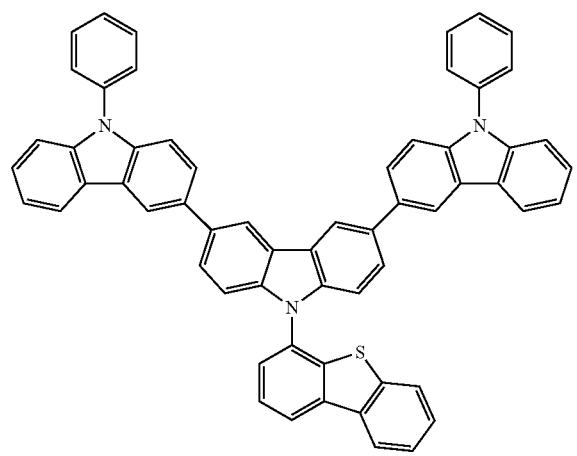
Compound 10
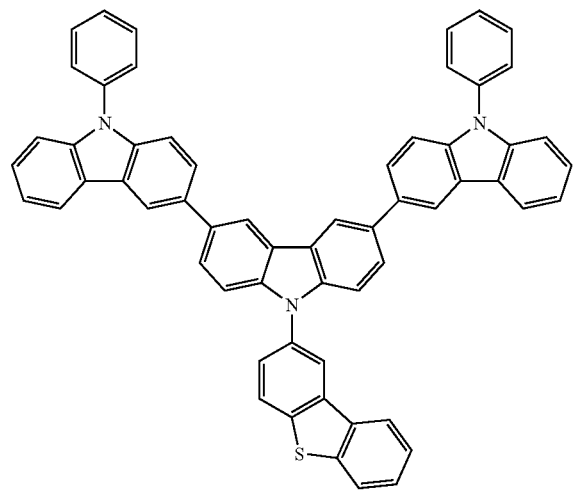
Compound 11
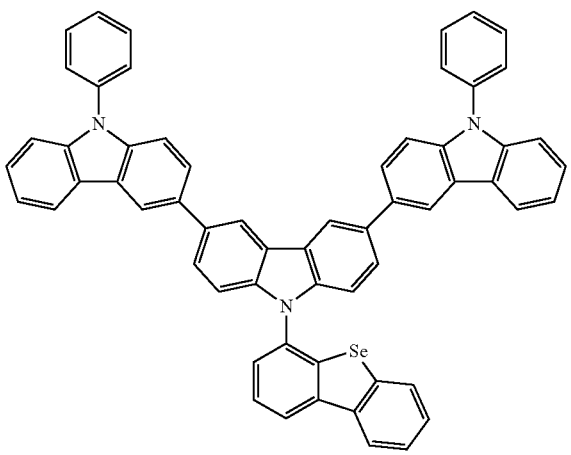
Compound 12
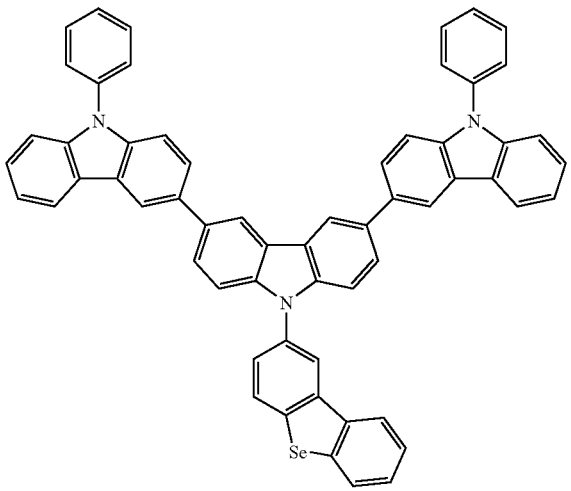
Compound 13
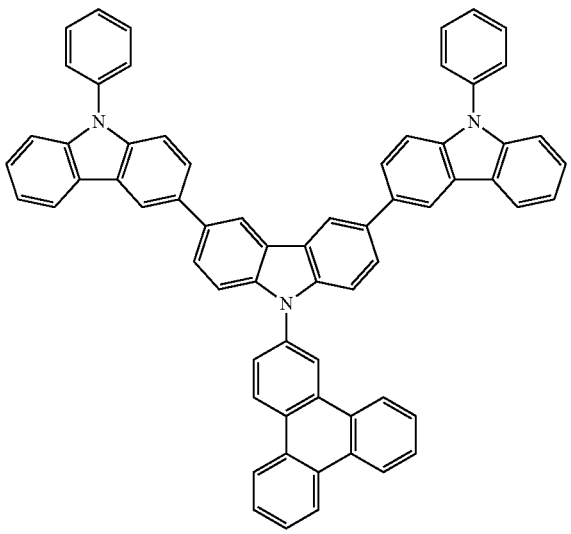

Compound 14

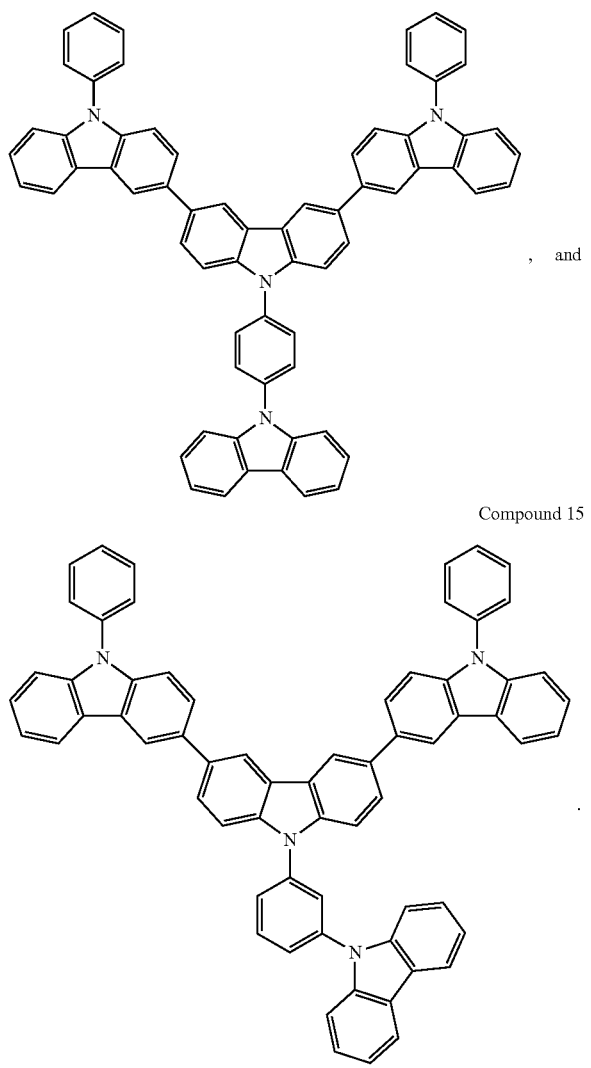

, and

Compound 15

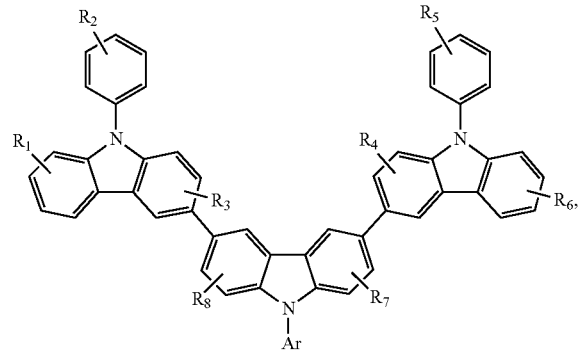

In one embodiment, a first device is provided. The first device comprises a first organic light emitting device, further comprising: an anode, a cathode, a hole injection layer disposed between the anode and the emissive layer, a first hole transport layer disposed between the hole injection layer and the emissive layer, and a second hole transport layer disposed between the first hole transport layer and the emissive layer, wherein the second hole transport layer comprises a compound of formula:

Formula II. In the compound of Formula II, Ar comprises aryl or heteroaryl, $R_1$ to $R_8$ independently represent mono, di, tri, tetra substitution, or no substitution, and $R_1$ to $R_8$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof.

In one embodiment, the second hole transport layer is disposed adjacent to the first hole transport layer. By "adjacent" it is meant that the second hole transport layer is physically in contact with the first hole transport layer. In one embodiment, the first hole transport layer is thicker than the second hole transport layer.

As used herein, a hole transporting layer (HTL) in an OLED can be disposed between the and anode and the emissive layer. It is preferred that the HTL is relatively hole conductive, which helps avoid high operating voltage. In order to achieve high hole conductivity, high hole mobility materials are used. These materials are usually triarylamine compounds. These compounds may have HOMO/LUMO levels and/or triplet energy which are not compatible with the emissive layer for optimum device performance and lifetime. On the other hand, in order to have an HTL with more compatible HOMO/LUMO levels and/or triplet energy, hole mobility may be compromised.

In order to achieve a low voltage, higher device performance and lifetime device, the introduction of a secondary hole transporting layer, in addition to the primary hole transporting layer has been demonstrated and shown to be effective. The primary hole transporting layer is largely responsible for hole transport. The secondary hole transporting layer, sandwiched between the primary hole transporting layer and the emissive layer, functions as a bridging layer. The thickness of the secondary hole transport layer is preferably low in order to not significantly increase the operating voltage. However, the hole injection from the secondary hole transporting layer to the emissive layer, charge confinement and exciton confinement between the secondary hole transporting layer and the emissive layer are controlled by the energy levels and single/triplet energy of the secondary hole transporting layer. Since the secondary hole transporting layer thickness is low, there is relatively little concern about the hole mobility. This allows for a higher flexibility in the design of materials with appropriate energy levels and single/triplet energy to function well with the emissive layer.

It has surprisingly been discovered that compounds of Formula I and II can be effectively used as materials in the secondary hole transporting layer, thereby improving the properties of the OLED devices in which they are incorporated.

In one embodiment, Ar is selected from the group consisting of:

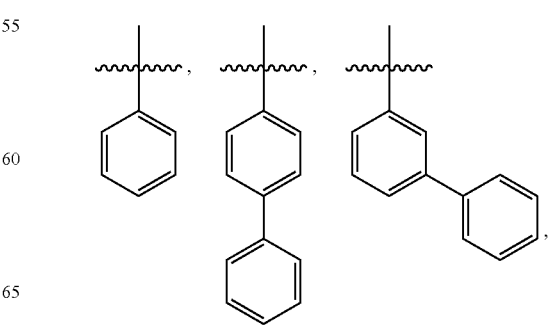

-continued
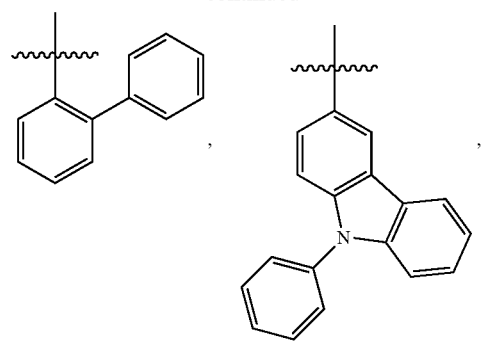
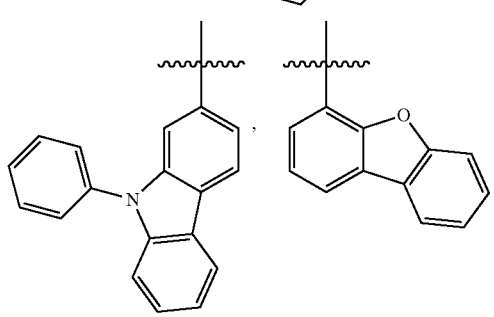
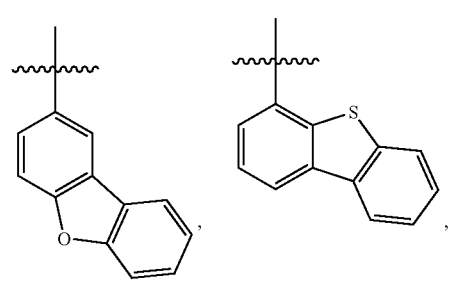
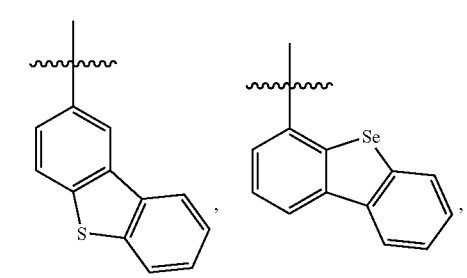
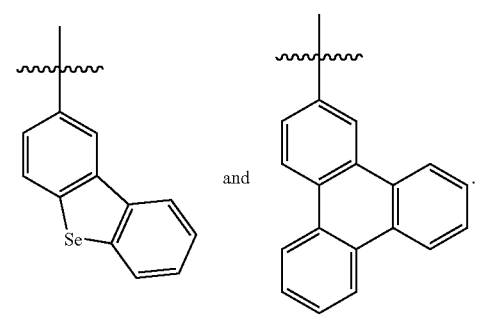 [SMILES: *c1ccc2[se]c3ccccc3c2c1 ; *c1ccc2c3ccccc3c3ccccc3c2c1]
In some embodiments, Ar is selected from the group consisting of:
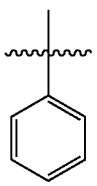
Ar-1
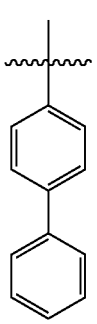
Ar-2
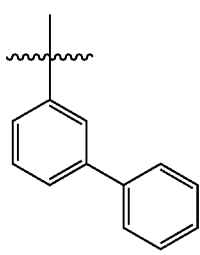
Ar-3
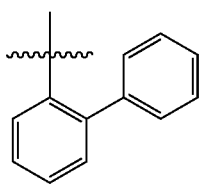
Ar-4
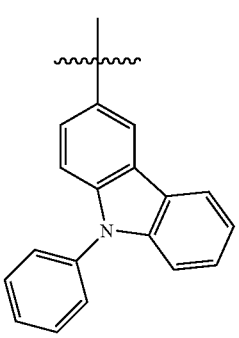
Ar-5

Ar-6 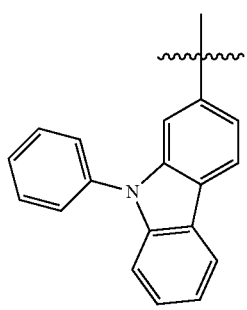
Ar-7 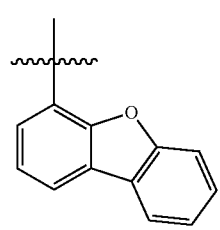
Ar-8 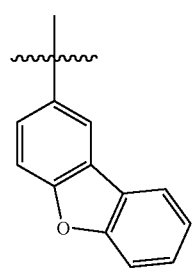
Ar-9 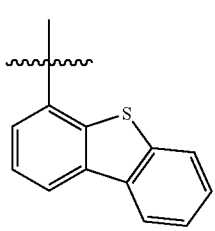
Ar-10 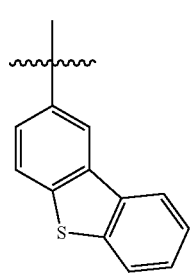
Ar-11 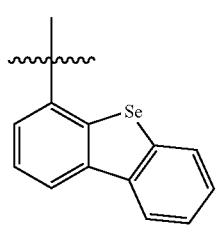
Ar-12 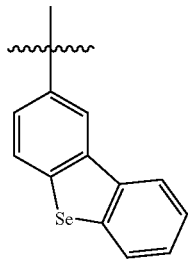
Ar-13 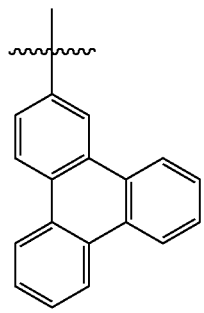
Ar-14 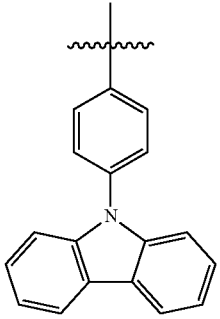
Ar-15 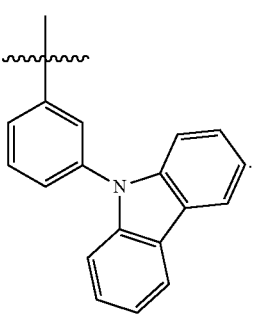
In some embodiments, the compound is selected from Compounds 1-15, whose structure is depicted in the table below:

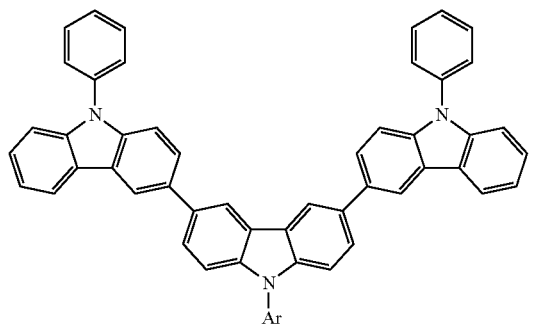

| Ar | Compound |
|---|---|
| Ar-1 | 1 |
| Ar-2 | 2 |
| Ar-3 | 3 |
| Ar-4 | 4 |
| Ar-5 | 5 |
| Ar-6 | 6 |
| Ar-7 | 7 |
| Ar-8 | 8 |
| Ar-9 | 9 |
| Ar-10 | 10 |
| Ar-11 | 11 |
| Ar-12 | 12 |
| Ar-13 | 13 |
| Ar-14 | 14 |
| Ar-15 | 15 |

In one embodiment, the compound has the formula:

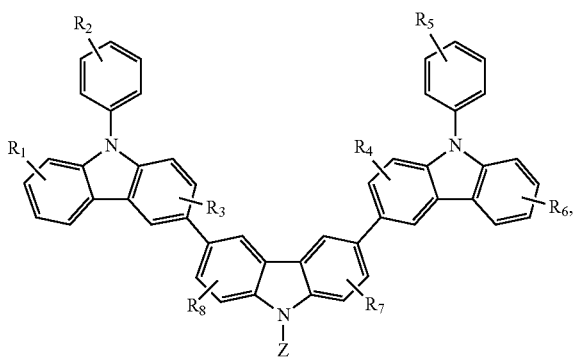

Formula I. In the compound of Formula I, Z is selected from the group consisting of:

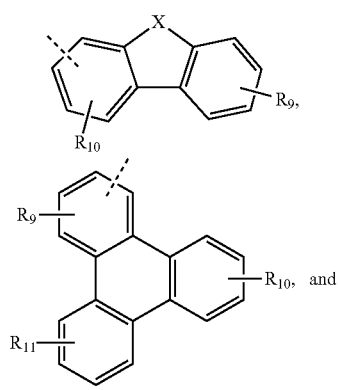

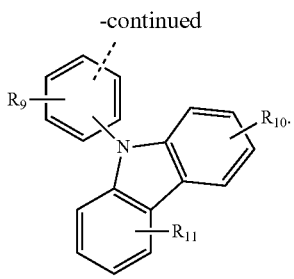

X is selected from the group consisting of NR, O, S, and Se, $R_9$, $R_{10}$, and $R_{11}$ independently represent mono, di, tri, tetra substitution, or no substitution, and R, $R_9$, $R_{10}$, and $R_{11}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, the first hole transport layer comprises a compound with the formula:

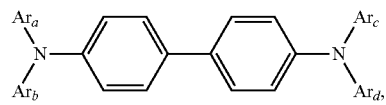

wherein $Ar_a$, $Ar_b$, $Ar_c$ and $Ar_d$ are independently selected from the group consisting of aryl and heteroaryl.

In one embodiment, the triplet energy of the compound of Formula II is higher than the emission energy of the emissive layer.

In one embodiment, the first device further comprises an emissive dopant comprising a transition metal complex having at least one ligand or part of the ligand if the ligand is more than bidentate selected from the group consisting of:

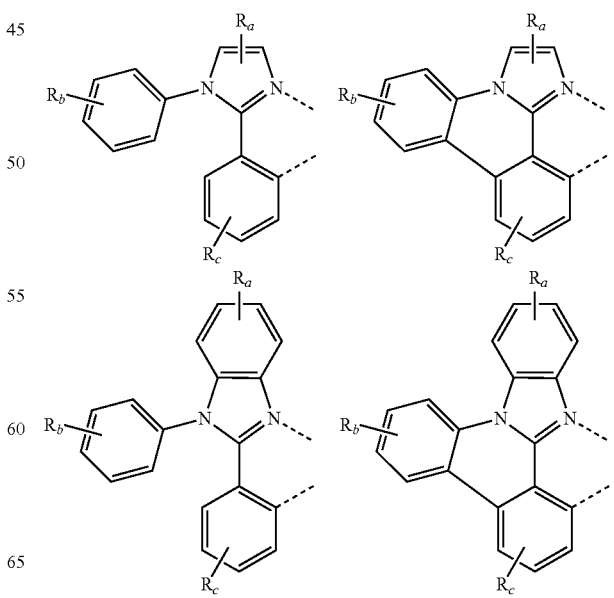

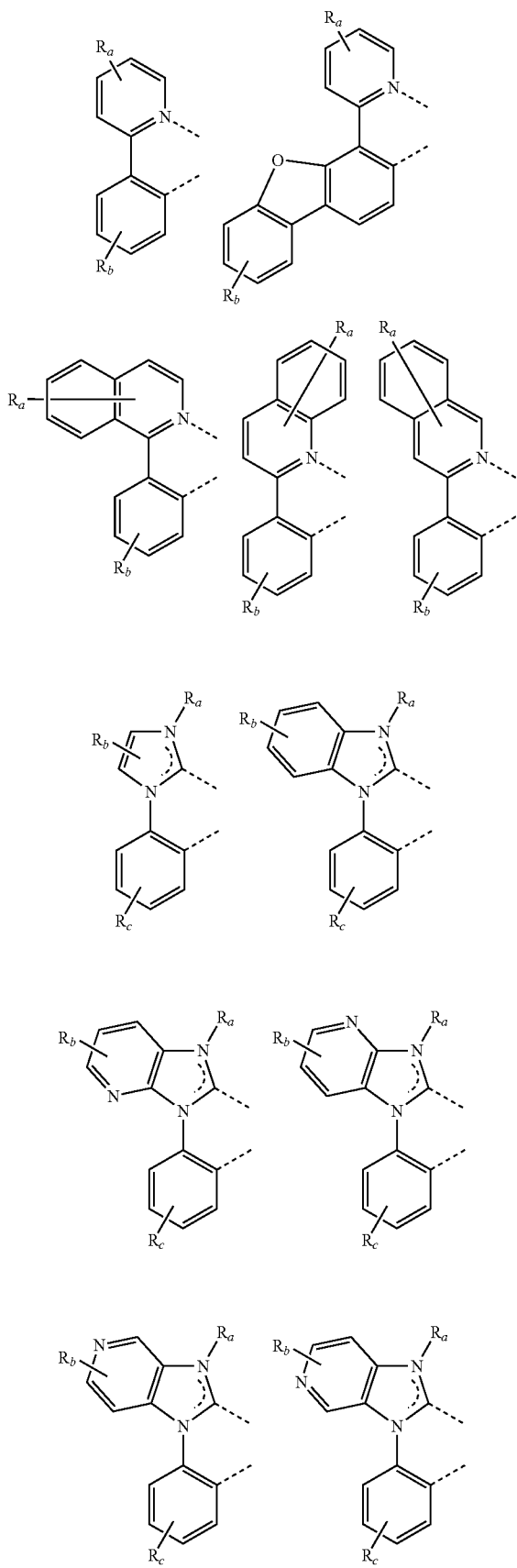
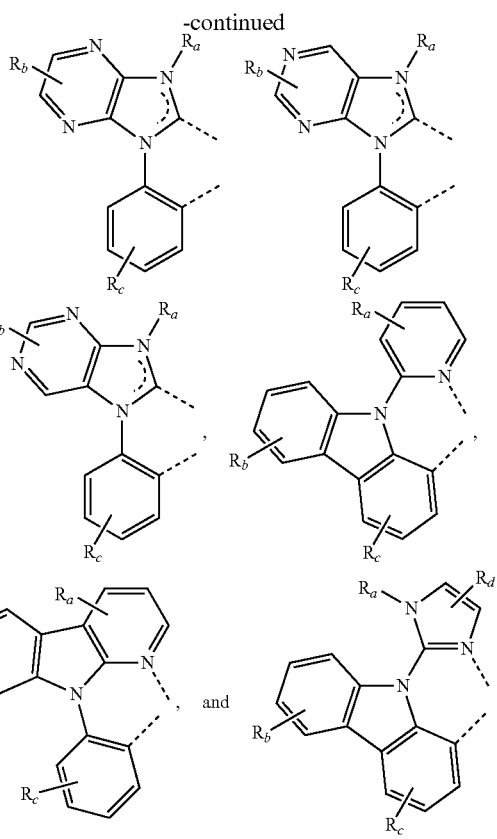

wherein $R_a$, $R_b$, $R_c$, and $R_d$ may represent mono, di, tri, or tetra substitution, or no substitution, wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

In one embodiment, the first device is a consumer product. In one embodiment, the first device is an organic light-emitting device. In one embodiment, the first device comprises a lighting panel.

In one embodiment, a first device comprising an organic light emitting device, further comprising: an anode, a cathode, a first organic layer disposed between the anode and the cathode; and wherein the first organic layer comprises a compound of formula:

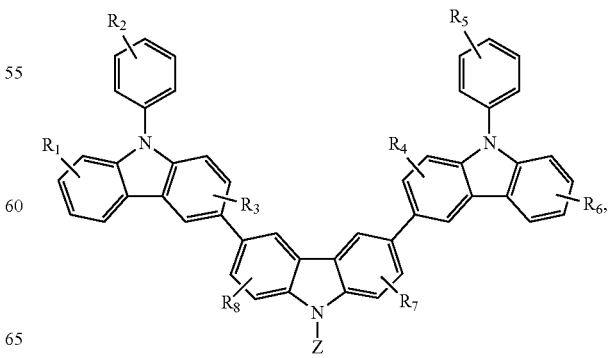

Formula I. In the compound of Formula I, Z is selected from the group consisting of:

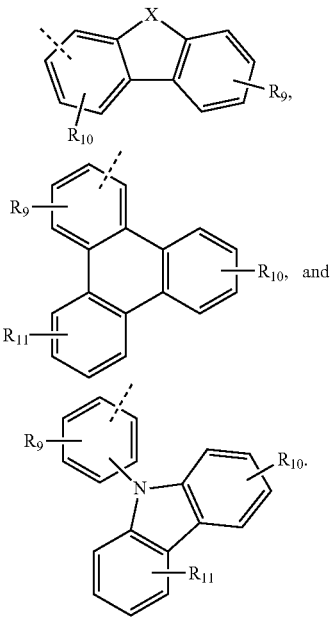

X is selected from the group consisting of NR, O, S, and Se, $R_1$ to $R_{11}$ independently represent mono, di, tri, tetra substitution, or no substitution; and R, and $R_1$ to $R_{11}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, the first organic layer is an emissive layer. In one embodiment, the emissive layer is a phosphorescent emissive layer.

DEVICE EXAMPLES

A device examples were fabricated by high vacuum ($<10^{-7}$ Torr) thermal evaporation (VTE). The anode electrode is ~800 Å of indium tin oxide (ITO). The cathode electrode consisted of 10 Å of LiF followed by 1,000 Å of Al. All devices were encapsulated with a glass lid sealed with an epoxy resin in a nitrogen glove box (<1 ppm of $H_2O$ and $O_2$) and a moisture getter was incorporated inside the package.

The organic stack of the Device Examples 1-5 in Table 1 consists of sequentially, from the ITO surface, 100 Å of LG101 (obtained from LG Chemical) as the hole injection layer (HIL), 500 Å (Table 1) of NPD as the primary hole transporting layer (HTL), 50 Å of the secondary hole transporting layer, 300 Å of Compound C or Compound D doped with 10% or 12% of phosphorescent emitter Compound E as the emissive layer (EML), 50 Å of Compound C or Compound D as the ETL2 and 450 Å of $Alq_3$ as the ETL1.

Device Example 6 was fabricated in the same way as in Device Examples 1-5 except that the EML layer has 3 components: 85% of Compound D, 10% of Compound 9.5% of Compound E.

Device Example 7-8 was fabricated in the same way as in Device Examples 6 except there was no secondary hole transporting layer, and the primary hole transporting layer thickness was increased to 550 Å to match the combined thickness of the primary and secondary hole transporting layers in the Device Examples 1-5.

Comparative Device Examples 1-3 were fabricated in the same way as Device Examples 1-5 except that there was no secondary hole transporting layer, and the primary hole transporting layer thickness was increased to 550 Å to match the combined thickness of the primary and secondary hole transporting layers in the Device Examples 1-5.

The organic stack of the Device Examples 9-13 and Comparative Device Example 4 in Table 2 consists of sequentially, from the ITO surface, 100 Å of LG101 as the hole injection layer (HIL), 200 Å (Table 1) of NPD as the hole transporting layer (HTL), 50 Å of the secondary hole transporting layer, 300 Å of Compound A or Compound B doped with 18% or 20% of phosphorescent emitter Compound F as the emissive layer (EML), 50 Å of Compound A as the ETL2 and 350 Å of $Alq_3$ as the ETL1.

Comparative Device Examples 4 was fabricated in the same way as Device Examples 9-13 except that there was no the secondary hole transporting layer, and the primary hole transporting layer thickness was increased to 250 Å to match the combined thickness of the primary and secondary hole transporting layers in the Device Examples.

The structures of the aforementioned device components are as follows:

Compound A

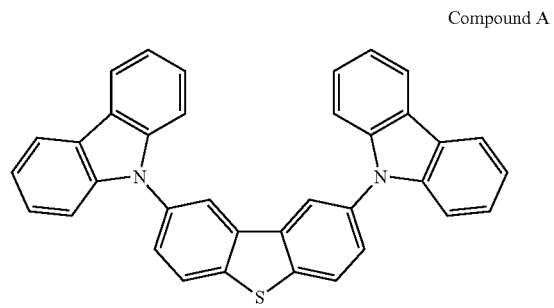

Compound B

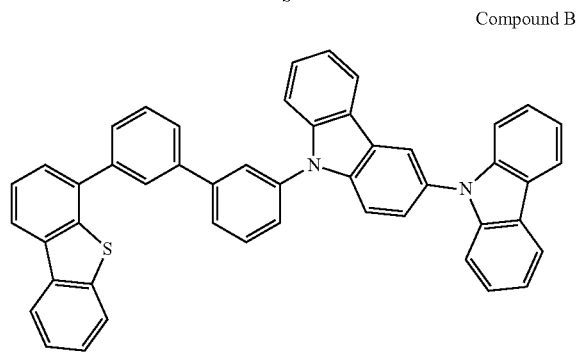

Compound C

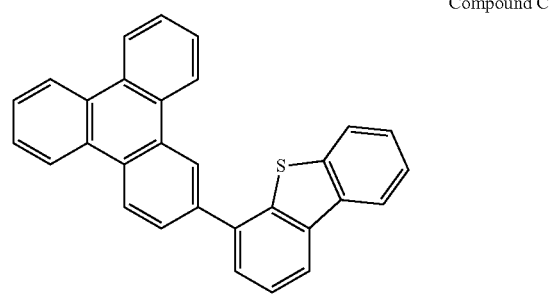

-continued

Compound D

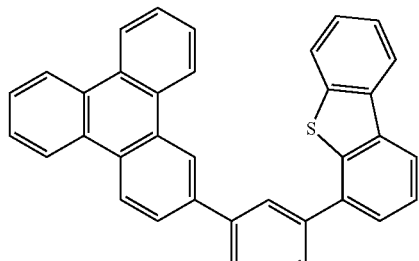

Compound E

Compound F

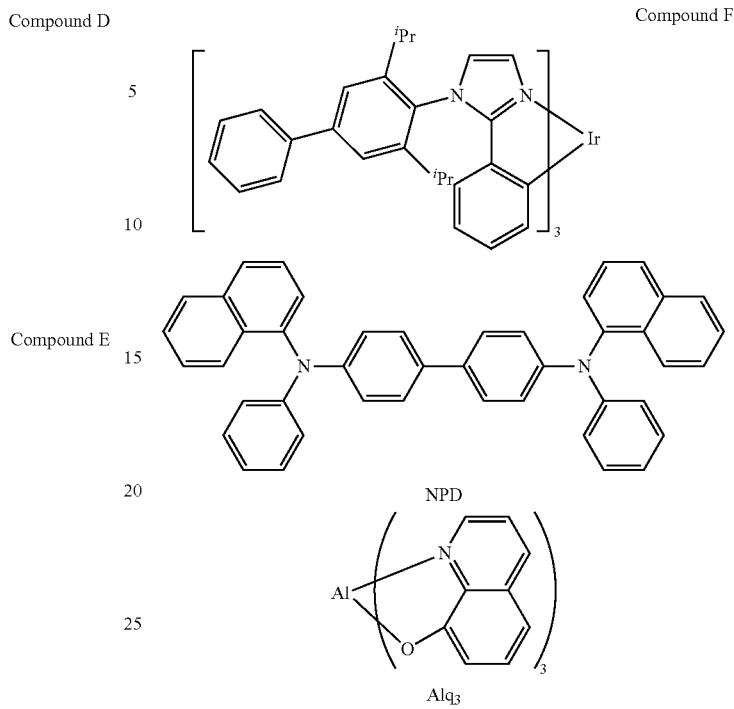

NPD

Alq₃

TABLE 1

Device performance and lifetime summary of green devices

| Example | Secondary HTL 50 Å | EML 300 Å | ETL2 50 Å | 1931 CIE x | y | Voltage [V] | LE [cd/A] | EQE [%] | PE [lm/W] | $L_0$ [cd/m$^2$] | $LT_{80}$ [h] |
|---|---|---|---|---|---|---|---|---|---|---|---|
| Device Example 1 | Cmpd 5 | Cmpd C:Cmpd E 10% | Cmpd C | 0.32 | 0.63 | 4.7 | 75 | 20.6 | 50.2 | 24884 | 340 |
| Device Example 2 | Cmpd 9 | Cmpd D:Cmpd E 10% | Cmpd D | 0.34 | 0.62 | 5.3 | 72 | 19.8 | 42.4 | 23396 | 330 |
| Device Example 3 | Cmpd 13 | Cmpd D:Cmpd E 12% | Cmpd D | 0.33 | 0.63 | 5.3 | 72.2 | 19.8 | 43.2 | 23762 | 250 |
| Device Example 4 | Cmpd 14 | Cmpd C:Cmpd E 12% | Cmpd C | 0.33 | 0.62 | 5 | 76.5 | 20.9 | 48.3 | 25911 | 266 |
| Device Example 5 | Cmpd 15 | Cmpd C:Cmpd E 10% | Cmpd C | 0.32 | 0.63 | 4.8 | 76.3 | 21 | 49.6 | 25722 | 303 |
| Device Example 6 | Cmpd 9 | Cmpd D:Cmpd 9 10%:Cmpd E 5% | Cmpd D | 0.33 | 0.62 | 5.8 | 69 | 19.1 | 37.6 | 22556 | 268 |
| Device Example 7 | none | Cmpd D:Cmpd 9 10%:Cmpd E 5% | Cmpd D | 0.32 | 0.63 | 5.8 | 60 | 16.5 | 32.7 | 17508 | 288 |
| Device Example 8 | none | Cmpd D:Cmpd 13 10%:Cmpd E 5% | Cmpd D | 0.32 | 0.63 | 5.5 | 62.8 | 17.3 | 35.8 | 19333 | 350 |
| Comparative Device Example 1 | none | Cmpd C:Cmpd E 12% | Cmpd C | 0.33 | 0.63 | 4.9 | 68.1 | 18.6 | 43.8 | 19596 | 290 |
| Comparative Device Example 2 | none | Cmpd D:Cmpd E 12% | Cmpd D | 0.32 | 0.63 | 5.2 | 64.3 | 17.6 | 38.8 | 18627 | 270 |
| Comparative Device Example 3 | none | Cmpd D:Cmpd E 10% | Cmpd D | 0.33 | 0.62 | 5.3 | 63 | 17.5 | 37.7 | 17863 | 295 |

TABLE 2

Device performance and lifetime summary of blue devices

| Example | Secondary HTL 50 Å | EML 300 Å | ETL2 50 Å | 1931 CIE x | y | Voltage [V] | LE [cd/A] | EQE [%] | PE [lm/W] | At J = 40 mA/cm2 $L_0$ [cd/m$^2$] | $LT_{80}$ [h] |
|---|---|---|---|---|---|---|---|---|---|---|---|
| Device Example 9 | Cmpd 14 | Cmpd A:Cmpd F 18% | Cmpd A | 0.18 | 0.39 | 6.1 | 54.5 | 24 | 28.2 | 9528 | 25 |
| Device Example 10 | Cmpd 15 | Cmpd B:Cmpd F 20% | Cmpd A | 0.18 | 0.40 | 5.9 | 58.3 | 25.3 | 30.9 | 10010 | 32 |
| Device Example 11 | Cmpd 5 | Cmpd B:Cmpd F 20% | Cmpd A | 0.18 | 0.40 | 5.7 | 57.9 | 25.2 | 31.7 | 9978 | 32 |
| Device Example 12 | Cmpd 13 | Cmpd B:Cmpd F 20% | Cmpd A | 0.18 | 0.40 | 6.5 | 46.1 | 20 | 22.3 | 7472 | 47 |
| Device Example 13 | Cmpd 9 | Cmpd A:Cmpd F 18% | Cmpd A | 0.18 | 0.39 | 5.7 | 51.3 | 22.7 | 28.1 | 8860 | 35 |
| Comparative Device Example 4 | none | Cmpd A:Cmpd F 18% | Cmpd A | 0.18 | 0.38 | 5.9 | 45.3 | 20.3 | 24.2 | 7357 | 52 |

(At L = 1000 cd/m$^2$ columns: Voltage, LE, EQE, PE)

As shown in Table 1, devices containing a secondary HTL (Device Examples 1-6) have higher efficiency (EQE~20%) compared to the devices without the secondary HTL (Device Examples 7-8 and Comparative Device Examples 1-3). Devices with the secondary HTL (Device Examples 1-6) also have higher lifetimes, similar to or better than the devices without the secondary HTL (Device Examples 7-8 and Comparative Device Examples 1-3). For example, $LT_{80}$ (the time required for the initial luminance ($L_0$) to drop to 80% of its initial value, at a constant current density of 40 mA/cm$^2$) is ~340 at $L_0$=24884 cd/m$^2$ for Device Example 1 compared to 290 h at $L_0$=19596 cd/m$^2$ for Comparative Device Example 1. At the same time, Device Example 1 has a higher efficiency (EQE=20.6%) compared to Comparative Device Example 1 (EQE=18.6%). The same trend is seen in comparing Device Example 2 and Comparative Device Example 3. Without being bound by theory, the improved efficiency and lifetime in the presence of the secondary HTL is believed to be due to the high triplet energy, providing improved exciton confinement, the presence of a dibenzothiophene or triphenylene group, providing a high triplet, charge stabilization moiety. The calculated triplet energies are summarized in Table 3.

TABLE 3

Calculated Triplet Energies of Compounds.

| Compound | Triplet energy (nm)[#] |
|---|---|
| NPD | 500 |
| Compound 5 | 417 |
| Compound 9 | 429 |
| Compound 13 | 447 |
| Compound 14 | 417 |
| Compound 15 | 417 |

[#]Based on DFT/B3LYP/6-31g(d) optimized geometry

In addition, compounds of Formula I and Formula II can improve device performance and lifetime when used as a host or co-dopant in the EML. When used as a codopant, the compounds of Formula I and Formula II can partially carry charge. This capability can allow the device to work at a lower phosphorescence emitter concentration. For example, Device Example 8 has 10% of Compound 13 and only 5% of the phosphorescent emitter in the EML whereas Comparative Device Example has 12% of the phosphorescent emitter in the EML. Yet, the efficiencies are similar and Device Example 8 lifetime is better. The $LT_{80}$ of Device Example 8 (EQE=17.5%) is 350 h at $L_0$=19333 cd/m$^2$ compared to 290 h at $L_0$=19596 cd/m$^2$ for Comparative Device Example 1 (EQE=18.6%). Furthermore, since the concentration of the phosphorescent emitter in the EML is reduced in Device Example 9, the CIE is more saturated-green.

In blue devices, the effect of having a secondary HTL on efficiency is very significant. For example, Device Example 9 has a much higher efficiency (EQE=25%) compared to Comparative Device Example 4 (EQE=20.3%). $LT_{80}$ of Device Example 9 is 25 h at $L_0$=9528 cd/m$^2$ compared to 50 h at $L_0$=7357 cd/m$^2$ for Comparative Device Example 1.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and slime derivatives; a metal oxide derivative, such as MoO$_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

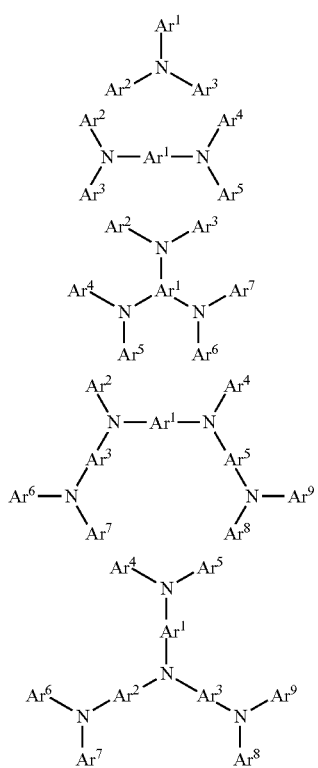

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof.

In one aspect, $Ar^1$ to $Ar^9$ is independently selected from the group consisting of:

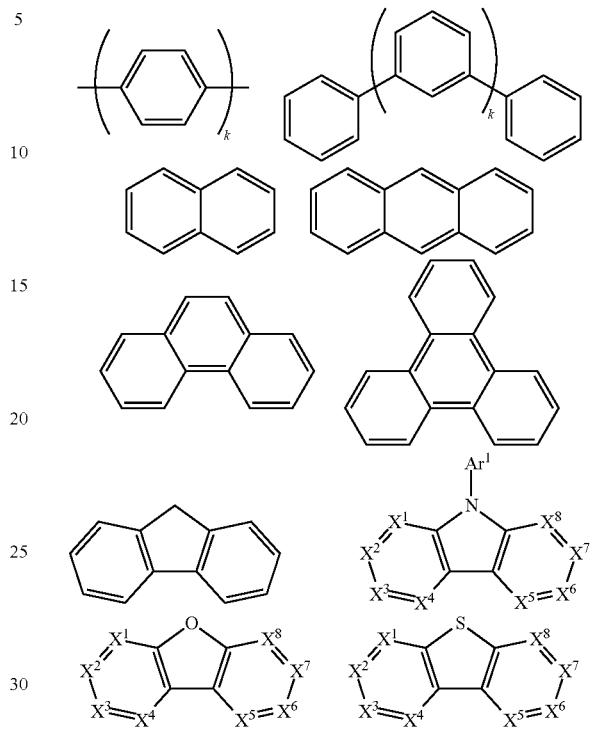

k is an integer from 1 to 20; $X^1$ to $X^8$ is C (including CH) or N; $Ar^1$ has the same group defined above.

Examples of metal complexes used in HIL or HTL include, but not limit to the following general formula:

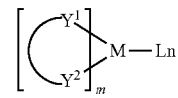

M is a metal, having an atomic weight greater than 40; ($Y^1$—$Y^2$) is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, ($Y^1$—$Y^2$) is a 2-phenylpyridine derivative.

In another aspect, ($Y^1$—$Y^2$) is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

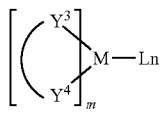

M is a metal; (Y³—Y⁴) is a bidentate ligand, Y³ and Y⁴ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

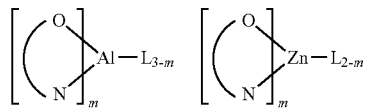

(O—N) is a bidentate ligand, having metal coordinated to atoms O and N.

In another aspect, M is selected from Ir and Pt.

In a further aspect, (Y³—Y⁴) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

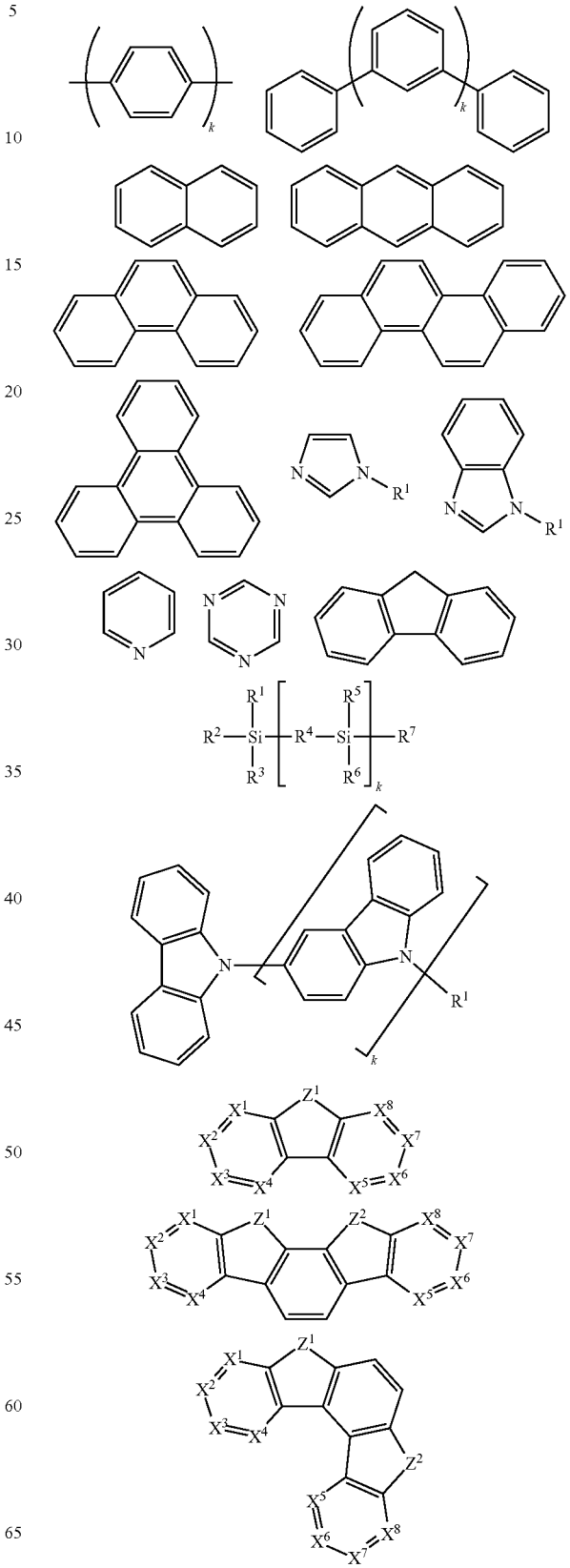

-continued

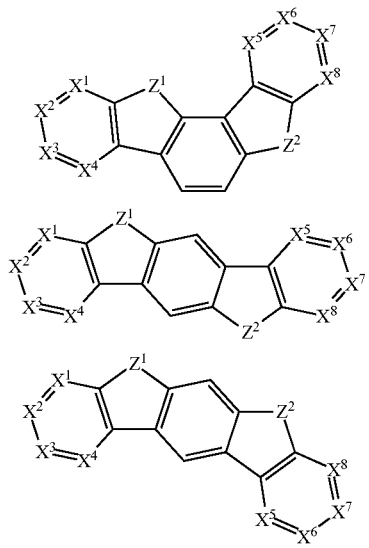

R$^1$ to R$^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphine, and combinations thereof, when it is aryl or heteroaryl, it has the similar definition as Ar's mentioned above.

k is an integer from 0 to 20.

X$^1$ to X$^8$ is selected from C (including CH) or N.

Z$^1$ and Z$^2$ is selected from NR$^1$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in BBL contains the same molecule or the same functional groups used as host described above.

In another aspect, compound used in HBL contains at least one of the following groups in the molecule:

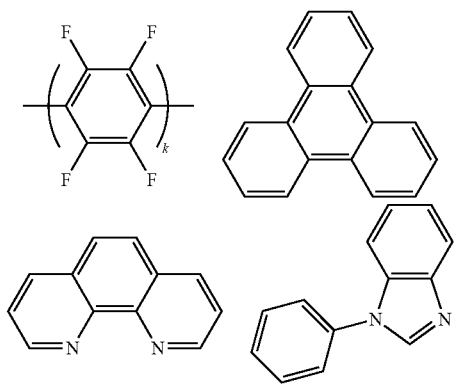

-continued

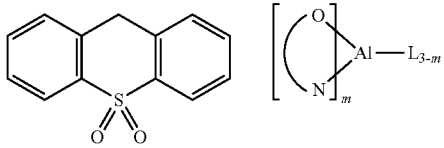

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

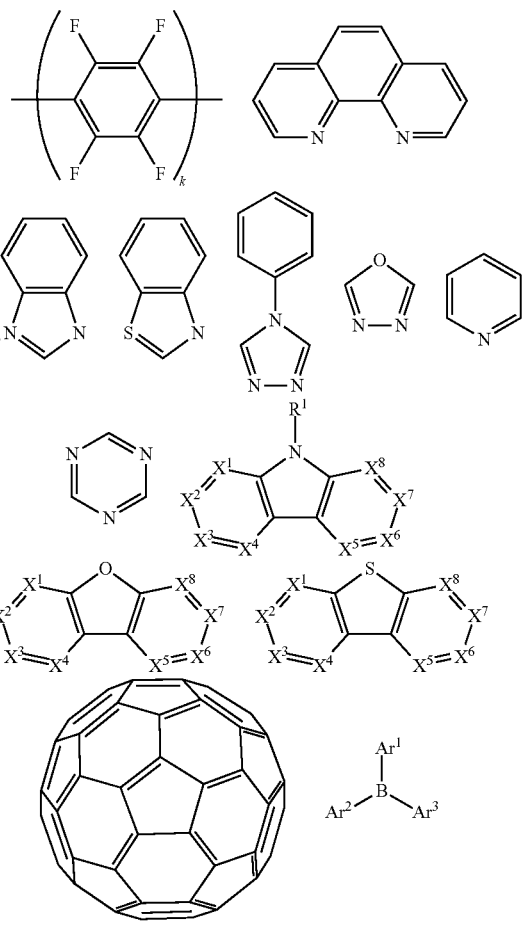

R$^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

Ar$^1$ to Ar$^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

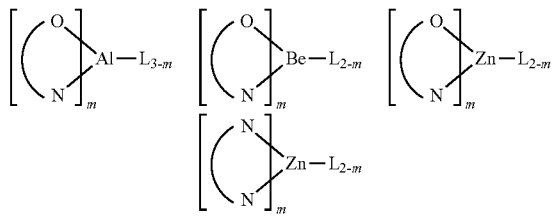

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 4 below. Table 4 lists non-limiting classes of materials, non-limiting examples of compounds for each class, and references that disclose the materials.

TABLE 4

| MATERIAL | EXAMPLES OF MATERIAL | PUBLICATIONS |
| --- | --- | --- |
| Hole injection materials | | |
| Phthalocyanine and porphryin compounds | [Cu phthalocyanine structure] | Appl. Phys. Lett. 69, 2160 (1996) |
| Starburst triarylamines | [starburst triarylamine structure] | J. Lumin. 72-74, 985 (1997) |
| $CF_x$ Fluorohydrocarbon polymer | $-\!\!+\!\!CH_xF_y\!\!+\!\!_n\!\!-$ | Appl. Phys. Lett. 78, 673 (2001) |
| Conducting polymers (e.g., PEDOT: PSS, polyaniline, polypthiophene) | [PEDOT:PSS structure] | Synth. Met. 87, 171 (1997) WO2007002683 |

TABLE 4-continued

| MATERIAL | EXAMPLES OF MATERIAL | PUBLICATIONS |
| --- | --- | --- |
| Phosphonic acid and silane SAMs | | US20030162053 |
| Triarylamine or polythiophene polymers with conductivity dopants | | EP1725079A1 |
| | | |
| Organic compounds with conductive inorganic compounds, such as molybdenum and tungsten oxides | + MoO$_x$ | US20050123751 SID Symposium Digest, 37, 923 (2006) WO2009018009 |

TABLE 4-continued
| MATERIAL | EXAMPLES OF MATERIAL | PUBLICATIONS |
|---|---|---|
| n-type semiconducting organic complexes | 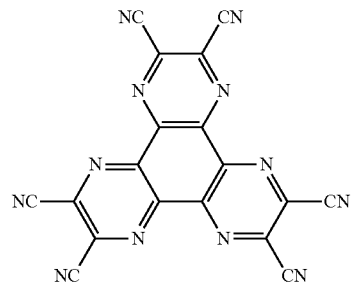 [SMILES: N#Cc1nc2c3nc(C#N)c(C#N)nc3c3nc(C#N)c(C#N)nc3c2nc1C#N] | US20020158242 |
| Metal organometallic complexes | 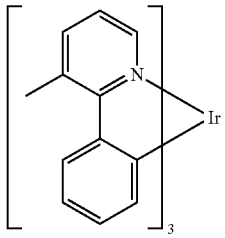 | US20060240279 |
| Cross-linkable compounds | 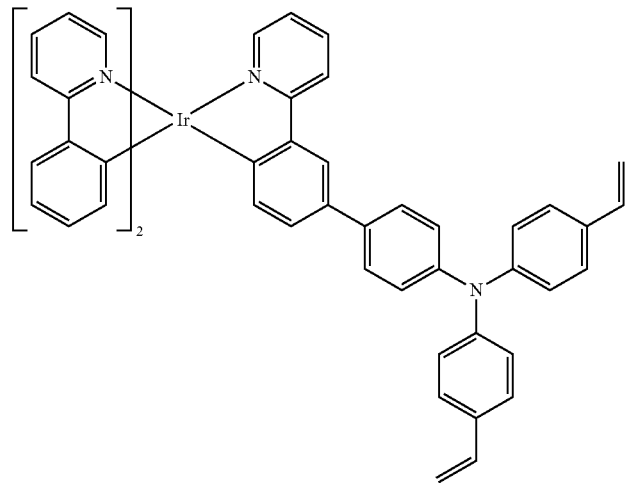 | US20080220265 |
| Polythiophene based polymers and copolymers | 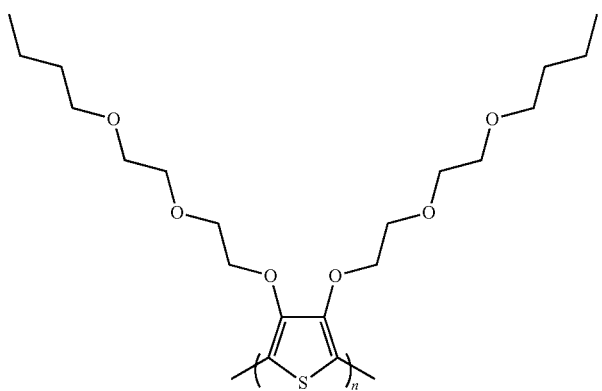 | WO2011075644<br>EP2350216 |

TABLE 4-continued
| MATERIAL | EXAMPLES OF MATERIAL | PUBLICATIONS |
|---|---|---|
| Hole transporting materials | | |
| Triarylamines (e.g., TPD, α-NPD) | 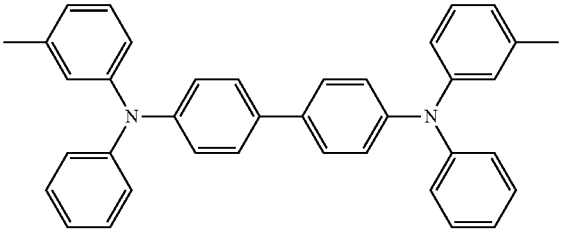 | Appl. Phys. Lett. 51, 913 (1987) |
| | 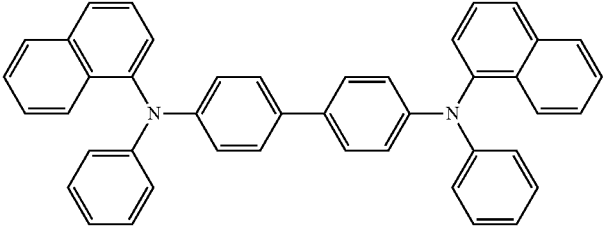 [SMILES: c1ccc(N(c2ccc(-c3ccc(N(c4ccccc4)c4cccc5ccccc45)cc3)cc2)c2cccc3ccccc23)cc1] | US5061569 |
| | 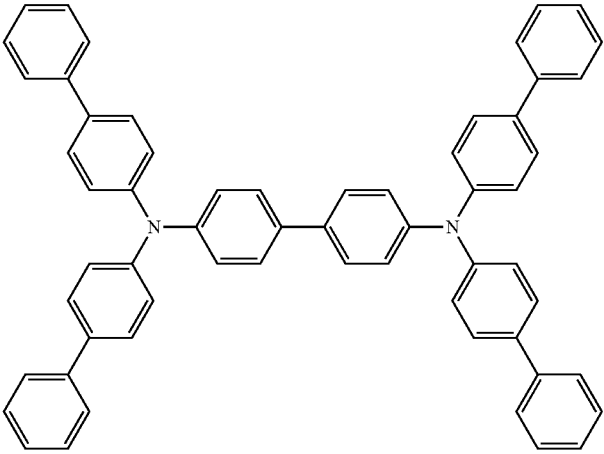 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 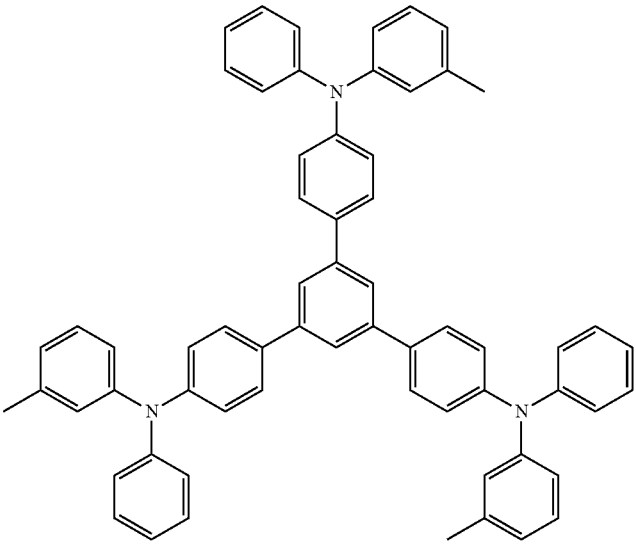 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 4-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997). |
| Arylamine carbazole compounds | | Adv. Mater. 6, 677 (1994), US20080124572 |

TABLE 4-continued
| MATERIAL | EXAMPLES OF MATERIAL | PUBLICATIONS |
| --- | --- | --- |
| Triarylamine with (di)benzothiophene/ (di)benzofuran | 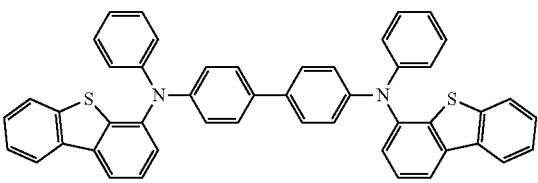 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 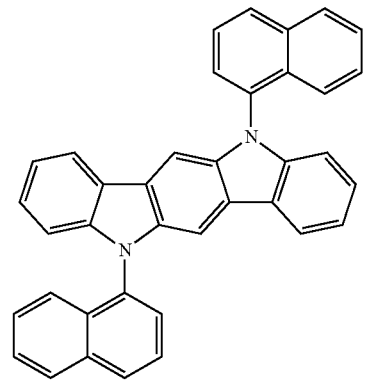 [SMILES: c1ccc2c(-n3c4ccccc4c4cc5c(cc43)c3ccccc3n5-c3cccc4ccccc34)cccc2c1] | Synth. Synth. Met. 111, 421 (2000) |
| Isoindole compounds | 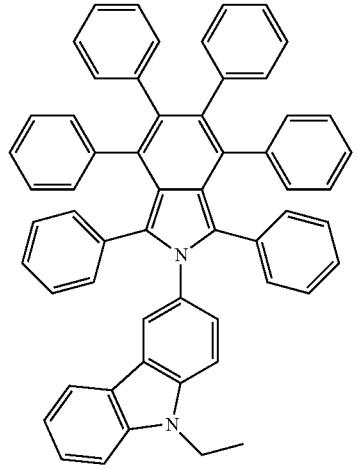 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 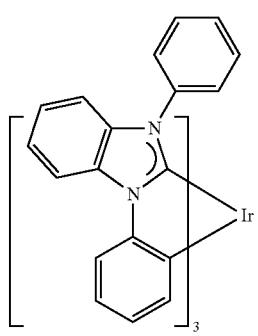 | US20080018221 |

TABLE 4-continued

| MATERIAL | EXAMPLES OF MATERIAL | PUBLICATIONS |
|---|---|---|
| | Phosphorescent OLED host materials Red hosts | |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 4-continued
| MATERIAL | EXAMPLES OF MATERIAL | PUBLICATIONS |
| --- | --- | --- |
| Aromatic fused rings | 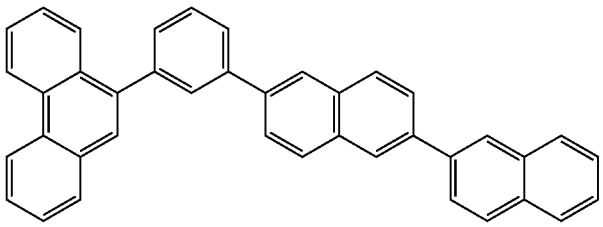 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 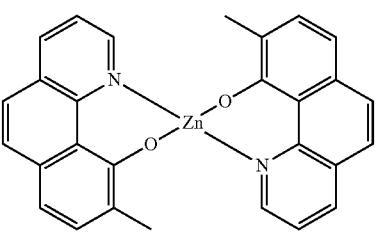 | WO2010056066 |
| Chrysene based compounds | 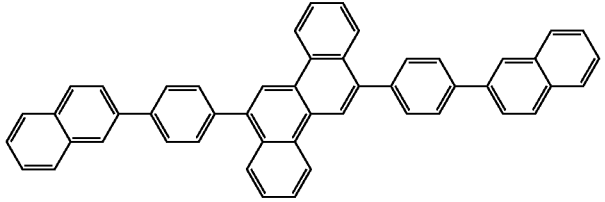 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
| Green hosts | | |
| Arylcarbazoles | 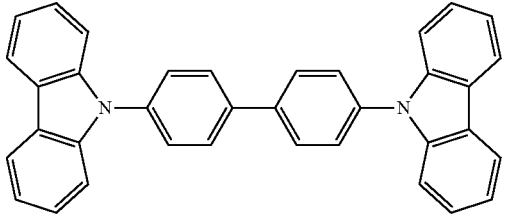 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 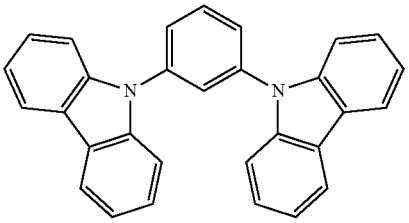 [SMILES: c1cc(-n2c3ccccc3c3ccccc32)cc(-n2c3ccccc3c3ccccc32)c1] | US20030175553 |
| | 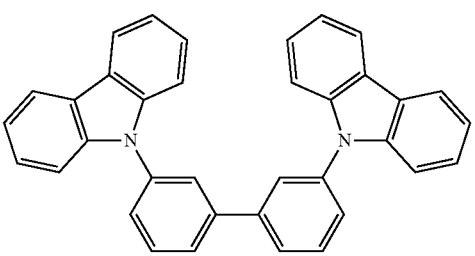 [SMILES: c1cc(-c2cccc(-n3c4ccccc4c4ccccc43)c2)cc(-n2c3ccccc3c3ccccc32)c1] | WO2001039234 |

TABLE 4-continued
| MATERIAL | EXAMPLES OF MATERIAL | PUBLICATIONS |
|---|---|---|
| Aryltriphenylene compounds | 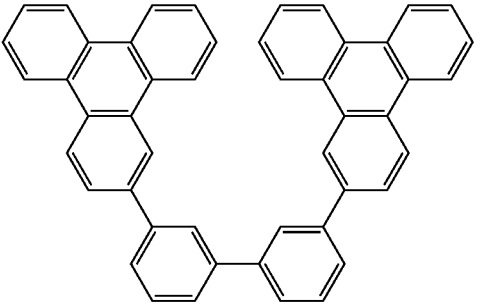 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 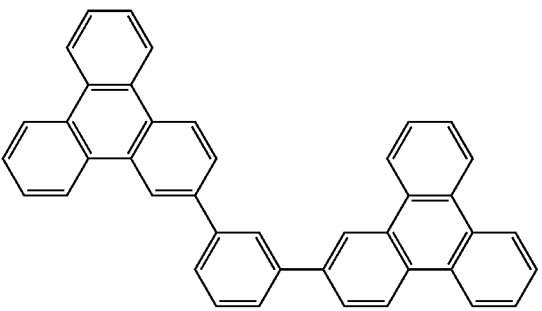 [SMILES: c1cc(-c2ccc3c4ccccc4c4ccccc4c3c2)cc(-c2ccc3c4ccccc4c4ccccc4c3c2)c1] | US20060280965 |
| | 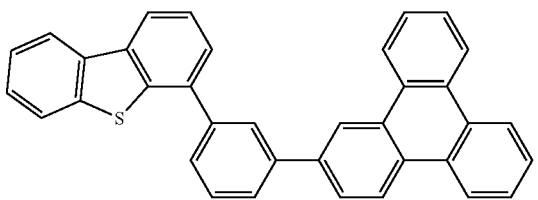 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 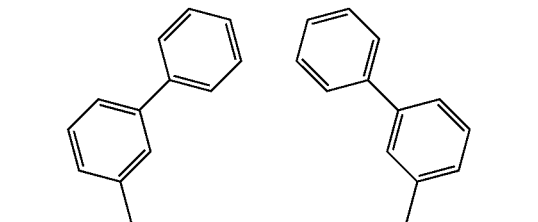 | US20090309488<br>US20090302743<br>US20100012931 |
| Donor acceptor type molecules | 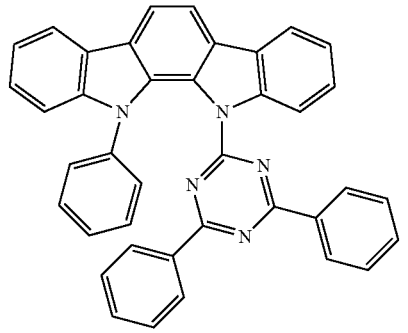 [SMILES: c1ccc(-c2nc(-c3ccccc3)nc(-n3c4ccccc4c4ccc5c6ccccc6n(-c6ccccc6)c5c43)n2)cc1] | WO2008056746 |

TABLE 4-continued
| MATERIAL | EXAMPLES OF MATERIAL | PUBLICATIONS |
|---|---|---|
| | 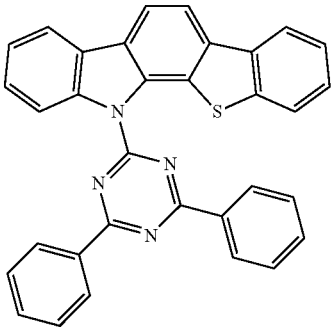 [SMILES: c1ccc(-c2nc(-c3ccccc3)nc(-n3c4ccccc4c4ccc5c6ccccc6sc5c43)n2)cc1] | WO2010107244 |
| Aza-carbazole/ DBT/DBF | 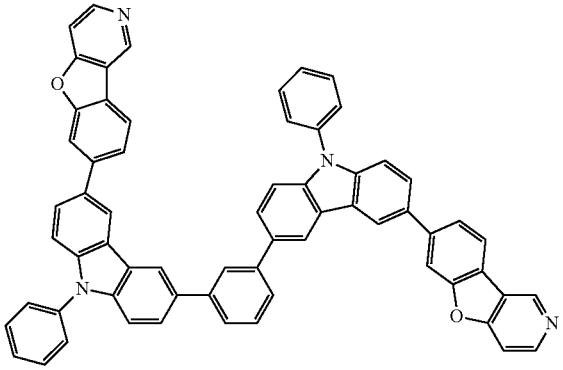 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 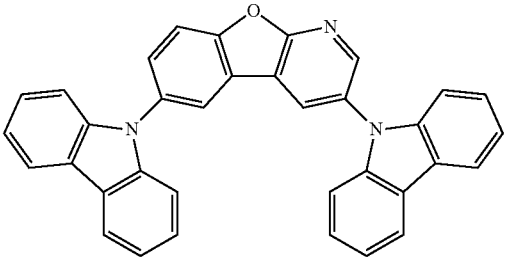 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 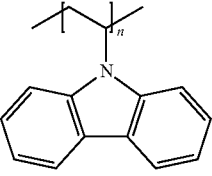 | Appl. Phys. Lett. 77, 2280 (2000) |
| Spirofluorene compounds | 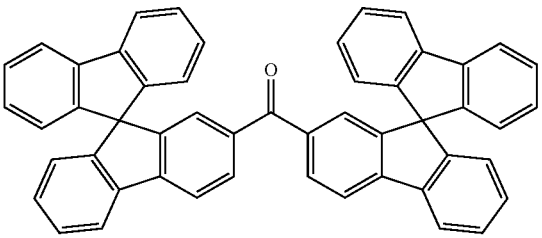 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 4-continued
| MATERIAL | EXAMPLES OF MATERIAL | PUBLICATIONS |
|---|---|---|
| Metal phenoxybenzooxazole compounds | 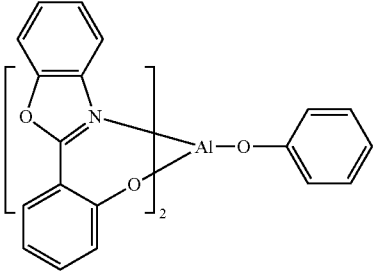 | WO2005089025 |
| | 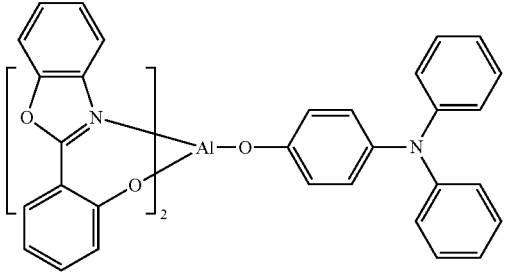 | WO2006132173 |
| | 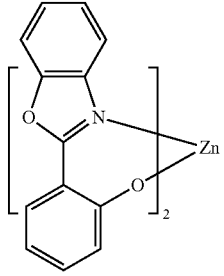 | JP200511610 |
| Spirofluorene-carbazole compounds | 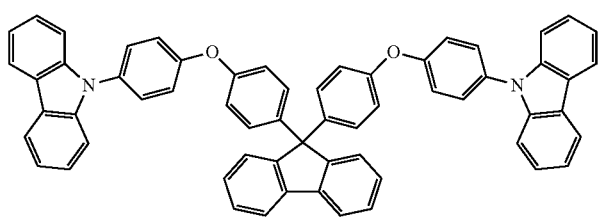 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 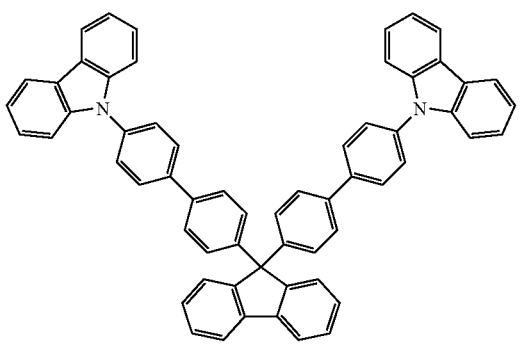 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |

TABLE 4-continued

| MATERIAL | EXAMPLES OF MATERIAL | PUBLICATIONS |
|---|---|---|
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 4-continued

| MATERIAL | EXAMPLES OF MATERIAL | PUBLICATIONS |
|---|---|---|
| Metal phenoxypyridine compounds | | WO2005030900 |
| Metal coordination complexes (e.g., Zn, Al with N^N ligands) | | US20040137268, US20040137267 |

Blue hosts

| | | |
|---|---|---|
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

TABLE 4-continued
| MATERIAL | EXAMPLES OF MATERIAL | PUBLICATIONS |
|---|---|---|
| | 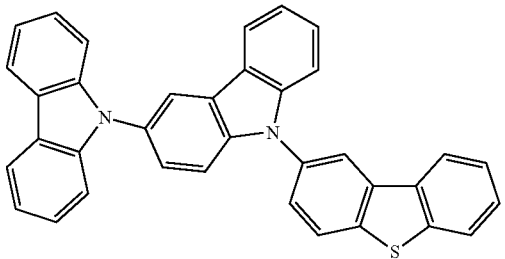 [SMILES: c1ccc2c(c1)sc1ccc(-n3c4ccccc4c4cc(-n5c6ccccc6c6ccccc65)ccc43)cc12] | WO2009086028 |
| | 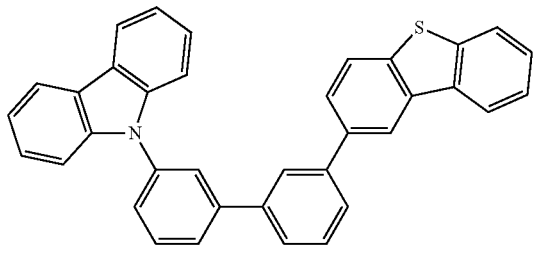 [SMILES: c1cc(-c2cccc(-n3c4ccccc4c4ccccc43)c2)cc(-c2ccc3sc4ccccc4c3c2)c1] | US20090030202, US20090017330 |
| | 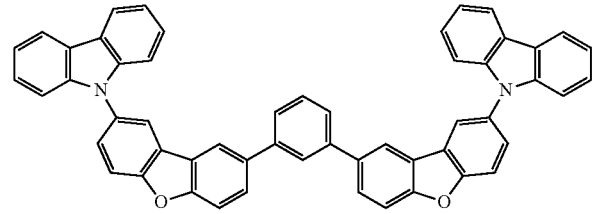 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 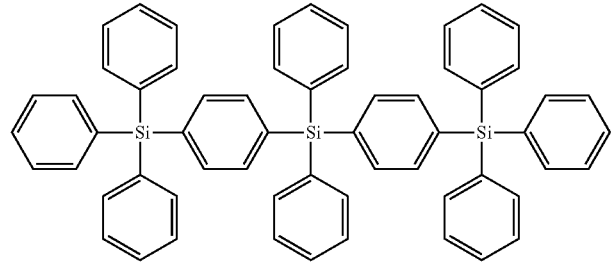 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 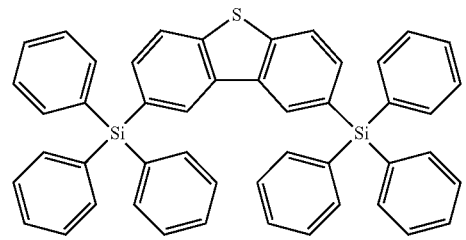 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/ Germanium aryl compounds | 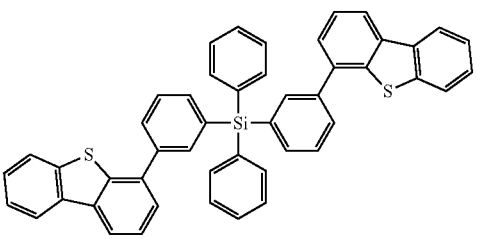 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |

TABLE 4-continued

| MATERIAL | EXAMPLES OF MATERIAL | PUBLICATIONS |
|---|---|---|
| Aryl benzoyl ester | | WO2006100298 |
| Carbazole linked by non-conjugated groups | | US20040115476 |
| Aza-carbazoles | | US20060121308 |
| High triplet metal organometallic complex | | US7154114 |

Phosphorescent dopants
Red dopants

| Heavy metal porphyrins (e.g., PtOEP) | | Nature 395, 151 (1998) |
|---|---|---|
| Iridium(III) organometallic complexes | | Appl. Phys. Lett. 78, 1622 (2001) |

TABLE 4-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

TABLE 4-continued

| MATERIAL | EXAMPLES OF MATERIAL | PUBLICATIONS |
|---|---|---|
| | | US20080261076<br>US20100090591 |
| | | US20070087321 |
| | | Adv. Mater. 19, 739 (2007) |
| | | WO2009100991 |
| | | WO2008101842 |

TABLE 4-continued

| MATERIAL | EXAMPLES OF MATERIAL | PUBLICATIONS |
|---|---|---|
|  |  | US7232618 |
| Platinum(II) organometallic complexes |  | WO2003040257 |
|  |  | US20070103060 |
| Osminum(III) complexes |  | Chem. Mater. 17, 3532 (2005) |
| Ruthenium(II) complexes |  | Adv. Mater. 17, 1059 (2005) |
| Rhenium (I), (II), and (III) complexes |  | US20050244673 |

TABLE 4-continued
| MATERIAL | EXAMPLES OF MATERIAL | PUBLICATIONS |
|---|---|---|
| | Green dopants | |
| Iridium(III) organometallic complexes | 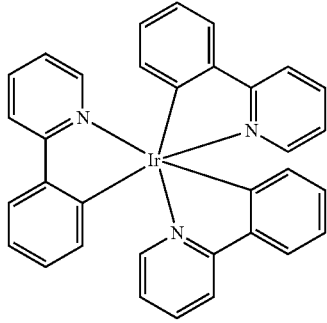<br>and its derivatives | Inorg. Chem. 40, 1704 (2001) |
| | 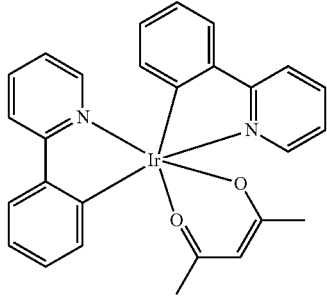 | US20020034656 |
| | 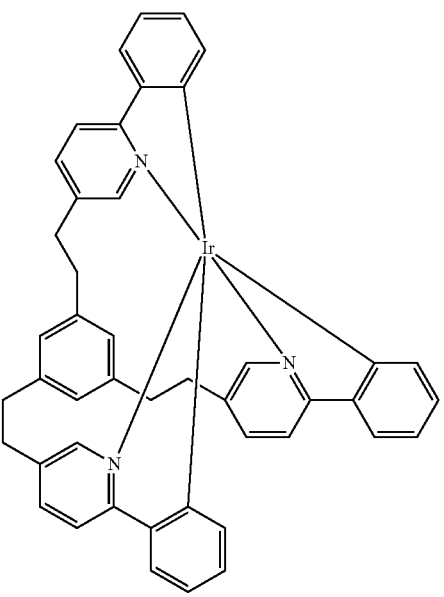 | US7332232 |

TABLE 4-continued

| MATERIAL | EXAMPLES OF MATERIAL | PUBLICATIONS |
|---|---|---|
| | | US20090108737 |
| | | WO2010028151 |
| | | EP1841834B |
| | | US20060127696 |
| | | US20090039776 |

TABLE 4-continued
| MATERIAL | EXAMPLES OF MATERIAL | PUBLICATIONS |
|---|---|---|
| | 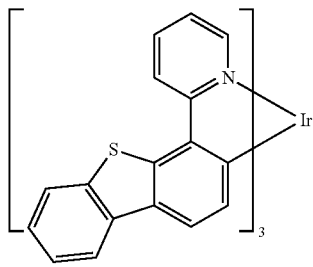 | US6921915 |
| | 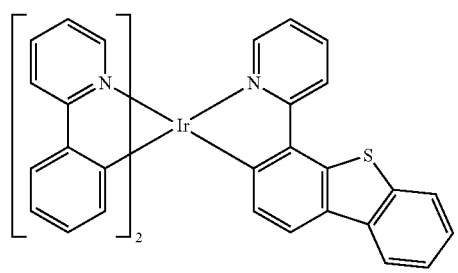 | US20100244004 |
| | 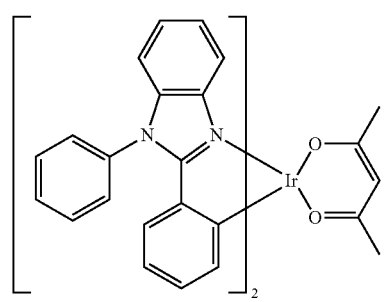 | US6687266 |
| | 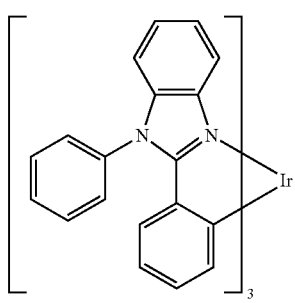 | Chem. Mater. 16, 2480 (2004) |
| | 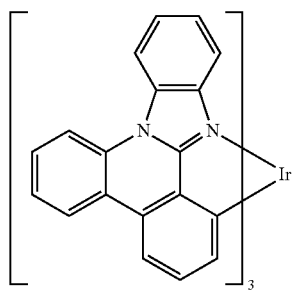 | US20070190359 |

TABLE 4-continued

| MATERIAL | EXAMPLES OF MATERIAL | PUBLICATIONS |
|---|---|---|
| | (structure) | US20060008670 JP2007123392 |
| | (structure) | WO2010086089, WO2011044988 |
| | (structure) | Adv. Mater. 16, 2003 (2004) |
| | (structure) | Angew. Chem. Int. Ed. 2006, 45, 7800 |
| | (structure) | WO2009050290 |
| | (structure) | US20090165846 |

TABLE 4-continued

| MATERIAL | EXAMPLES OF MATERIAL | PUBLICATIONS |
|---|---|---|
| | | US20080015355 |
| | | US20010015432 |
| | | US20100295032 |
| Monomer for polymeric metal organometallic compounds | | US7250226, US7396598 |
| Pt(II) organometallic complexes, including polydentated ligands | | Appl. Phys. Lett. 86, 153505 (2005) |

TABLE 4-continued
| MATERIAL | EXAMPLES OF MATERIAL | PUBLICATIONS |
|---|---|---|
| | 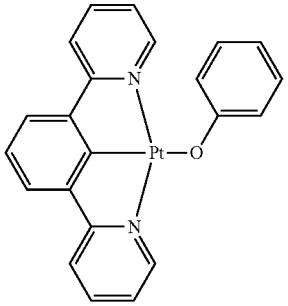 | Appl. Phys. Lett. 86, 153505 (2005) |
| | 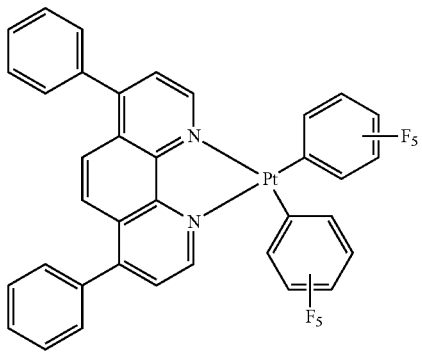 | Chem. Lett. 34, 592 (2005) |
| | 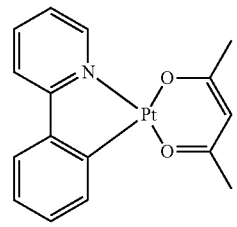 | WO2002015645 |
| | 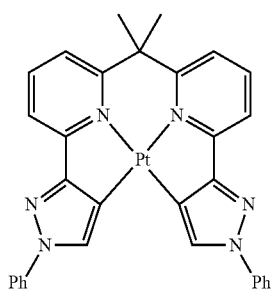 | US20060263635 |
| | 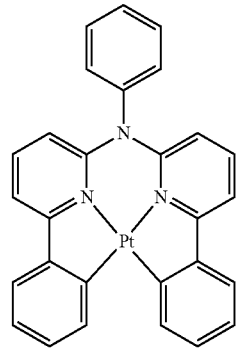 | US20060182992<br>US20070103060 |

TABLE 4-continued
| MATERIAL | EXAMPLES OF MATERIAL | PUBLICATIONS |
|---|---|---|
| Cu complexes | 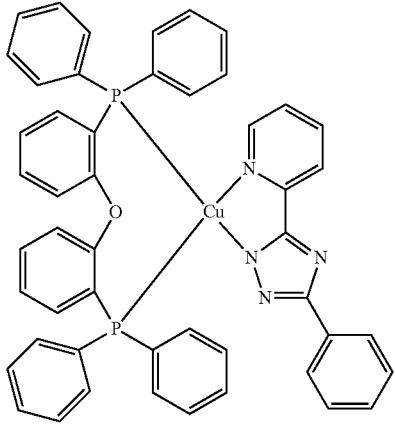 | WO2009000673 |
| | 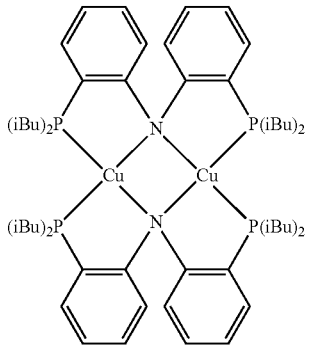 | US20070111026 |
| Gold complexes | 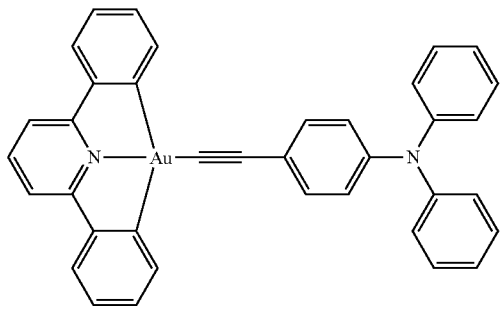 | Chem. Commun. 2906 (2005) |
| Rhenium(III) complexes | 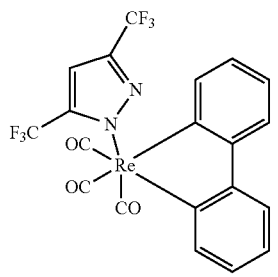 | Inorg. Chem. 42, 1248 (2003) |

TABLE 4-continued

| MATERIAL | EXAMPLES OF MATERIAL | PUBLICATIONS |
| --- | --- | --- |
| Osmium(II) complexes | | US7279704 |
| Deuterated organometallic complexes | | US20030138657 |
| Organometallic complexes with two or more metal centers | | US20030152802 |
| | | US7090928 |

TABLE 4-continued
| MATERIAL | EXAMPLES OF MATERIAL | PUBLICATIONS |
|---|---|---|
| Blue dopants | | |
| Iridium(III) organometallic complexes | 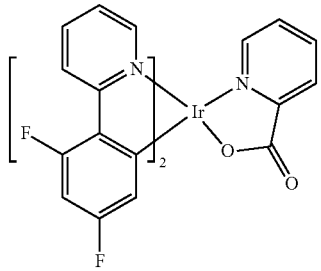 | WO2002002714 |
| | 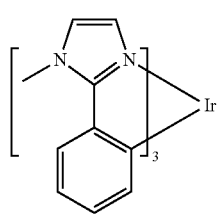 | WO2006009024 |
| | 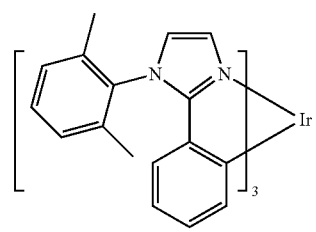 | US20060251923<br>US20110057559<br>US20110204333 |
| | 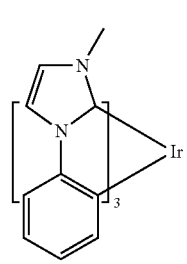 | US7393599,<br>WO2006056418,<br>US20050260441,<br>WO2005019373 |
| | 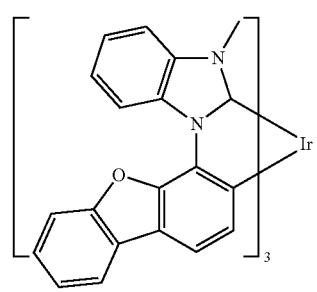 | US7534505 |
| | 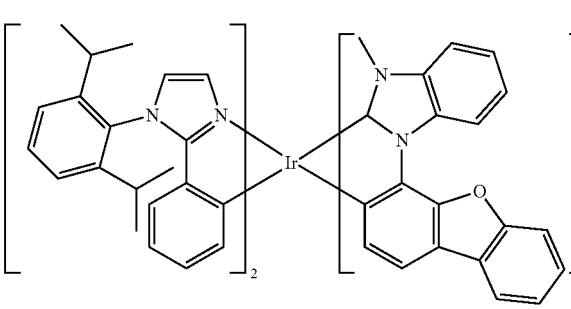 | WO2011051404 |

TABLE 4-continued

| MATERIAL | EXAMPLES OF MATERIAL | PUBLICATIONS |
|---|---|---|
| | | US7445855 |
| | | US20070190359, US20080297033 US20100148663 |
| | | US7338722 |
| | | US20020134984 |
| | | Angew. Chem. Int. Ed. 47, 1 (2008) |

TABLE 4-continued

| MATERIAL | EXAMPLES OF MATERIAL | PUBLICATIONS |
|---|---|---|
| | | Chem. Mater. 18, 5119 (2006) |
| | | Inorg. Chem. 46, 4308 (2007) |
| | | WO2005123873 |
| | | WO2005123873 |
| | | WO2007004380 |

TABLE 4-continued
| MATERIAL | EXAMPLES OF MATERIAL | PUBLICATIONS |
|---|---|---|
| | 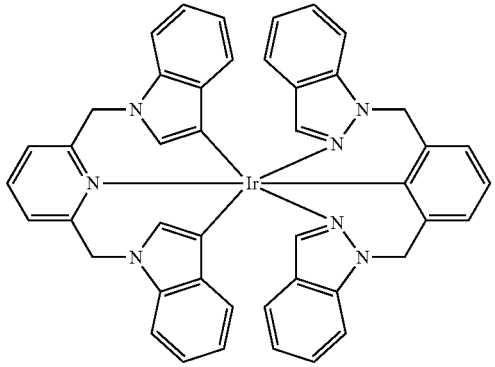 | WO2006082742 |
| Osmium(II) complexes | 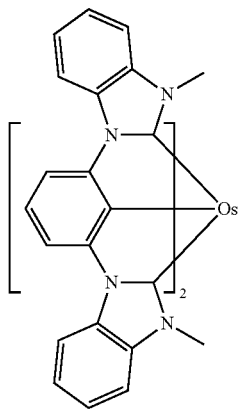 | US7279704 |
| | 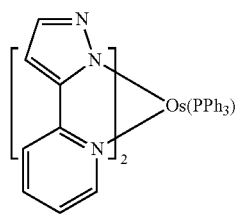 | Organometallics 23, 3745 (2004) |
| Gold complexes | 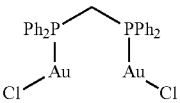 | Appl. Phys. Lett. 74, 1361 (1999) |
| Platinum(II) complexes | 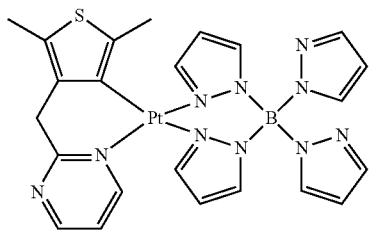 | WO2006098120, WO2006103 874 |

TABLE 4-continued

| MATERIAL | EXAMPLES OF MATERIAL | PUBLICATIONS |
|---|---|---|
| Pt tetradentate complexes with at least one metal-carbene bond | 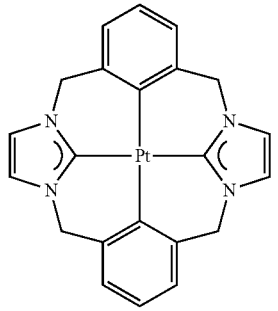 | US7655323 |

Exciton/hole blocking layer materials

| MATERIAL | EXAMPLES OF MATERIAL | PUBLICATIONS |
|---|---|---|
| Bathocuprine compounds (e.g., BCP, BPhen) | 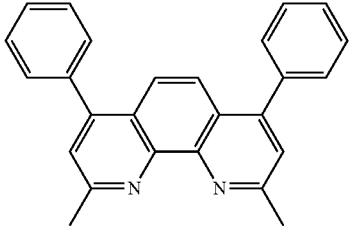 [SMILES: Cc1cc(-c2ccccc2)c2ccc3c(-c4ccccc4)cc(C)nc3c2n1] | Appl. Phys. Lett. 75, 4 (1999) |
|  | 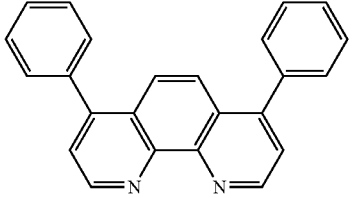 [SMILES: c1ccc(-c2ccnc3c2ccc2c(-c4ccccc4)ccnc23)cc1] | Appl. Phys. Lett. 79, 449 (2002) |
| Metal 8-hydroxyquinolates (e.g., BAlq) | 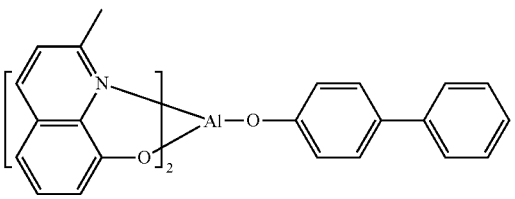 | Appl. Phys. Lett. 81, 162 (2002) |
| 5-member ring electron deficient heterocycles such as triazole, oxadiazole, imidazole, benzoimidazole | 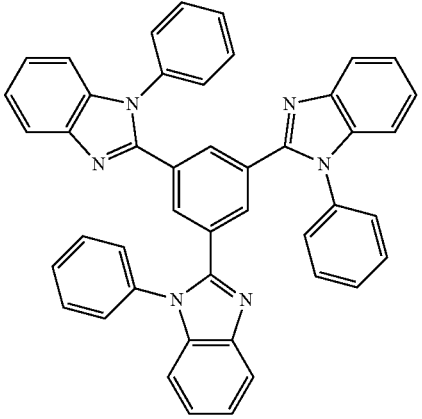 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 4-continued

| MATERIAL | EXAMPLES OF MATERIAL | PUBLICATIONS |
|---|---|---|
| Triphenylene compounds | | US20050025993 |
| Fluorinated aromatic compounds | | Appl. Phys. Lett. 79, 156 (2001) |
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |

TABLE 4-continued

| MATERIAL | EXAMPLES OF MATERIAL | PUBLICATIONS |
| --- | --- | --- |
| | Electron transporting materials | |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987)<br>US7230107 |

TABLE 4-continued

| MATERIAL | EXAMPLES OF MATERIAL | PUBLICATIONS |
|---|---|---|
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 4-continued

| MATERIAL | EXAMPLES OF MATERIAL | PUBLICATIONS |
| --- | --- | --- |
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc 122, 1832 (2000) |
| Fullerene (e.g., C60) | | US20090101870 |
| Triazine complexes | | US20040036077 |

| MATERIAL | EXAMPLES OF MATERIAL | PUBLICATIONS |
|---|---|---|
| Zn (N^N) complexes | | US6528187 |

Experimental

Chemical abbreviations used throughout this document are as follows: Cy is cyclohexyl, dba is dibenzylideneacetone, EtOAc is ethyl acetate, DME is dimethoxyethane, dppe is 1,2-bis(diphenylphosphino)ethane, THF is tetrahydrofuran, DMF is dimethylformamide, DCM is dichloromethane, S-Phos is dicyclohexyl(2',6'-dimethoxy-[1,1'-biphenyl]-2-yl)phosphine, Tf is trifluoromethylsulfonate. Unless specified otherwise, references to degassing a particular solvent refer to saturating the solvent sufficiently with dry nitrogen gas (by bubbling it in the solvent) to substantially remove gaseous oxygen from the solvent.

Synthesis of 3,6-bis(9-phenylcarbazol-3-yl)carbazole

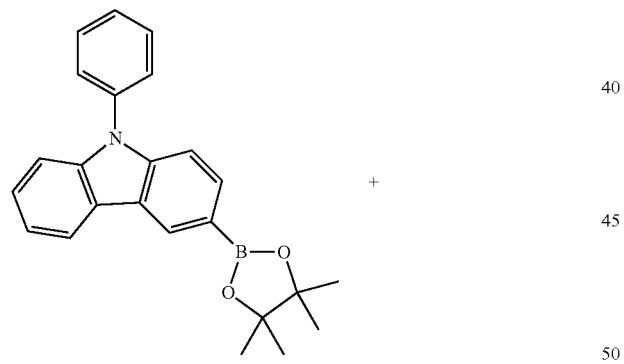

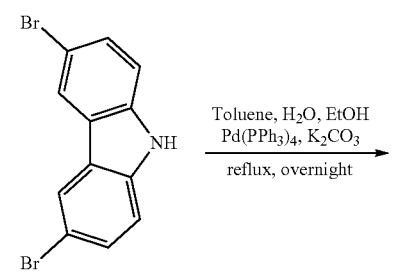

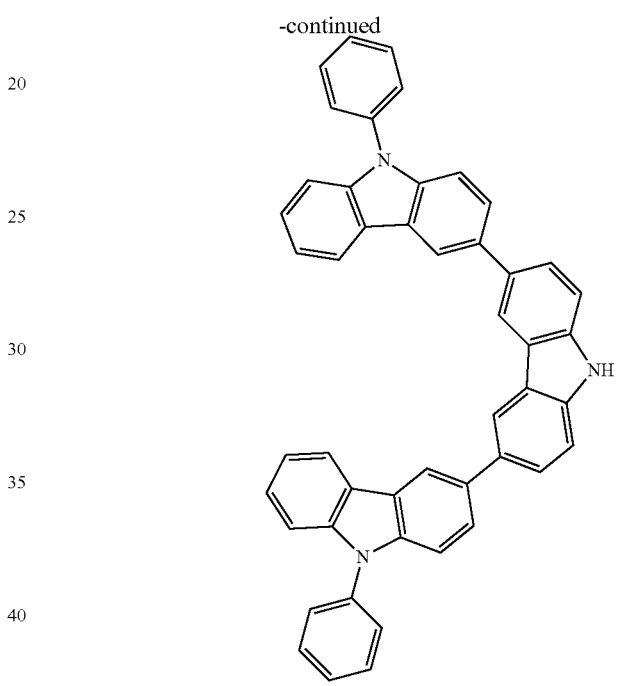

A solution of 9-phenyl-3-(4,4,5,5-tetramethyl-1,3,2-dioxaborolan-2-yl)carbazole (7.1 g, 19.2 mmol), 3,6-dibromo-9H-carbazole (2.6 g, 8.0 mmol), $K_2CO_3$ (11.0 g, 79.7 mmol) in toluene (120 mL), water (40 mL) and EtOH (40 mL) was bubbled for 30 minutes with nitrogen. Then, Pd(PPh$_3$)$_4$ (0.9 g, 0.8 mmol) was added. The mixture was bubbled with nitrogen for 15 minutes and refluxed for 10 hours, after which bromobenzene (0.9 mL, 8.6 mmol) was added. The resultant mixture was refluxed for 6 hours. After cooling, the reaction mixture was extracted with $CH_2Cl_2$ and dried with $MgSO_4$. The solvent was removed in vacuo and the residue was purified by flash chromatography using 40-60% $CH_2Cl_2$/hexane to afford 3,6-bis(9-phenylcarbazol-3-yl)carbazole (3.4 g, 65% yield) as a white solid.

Synthesis of Compound 5

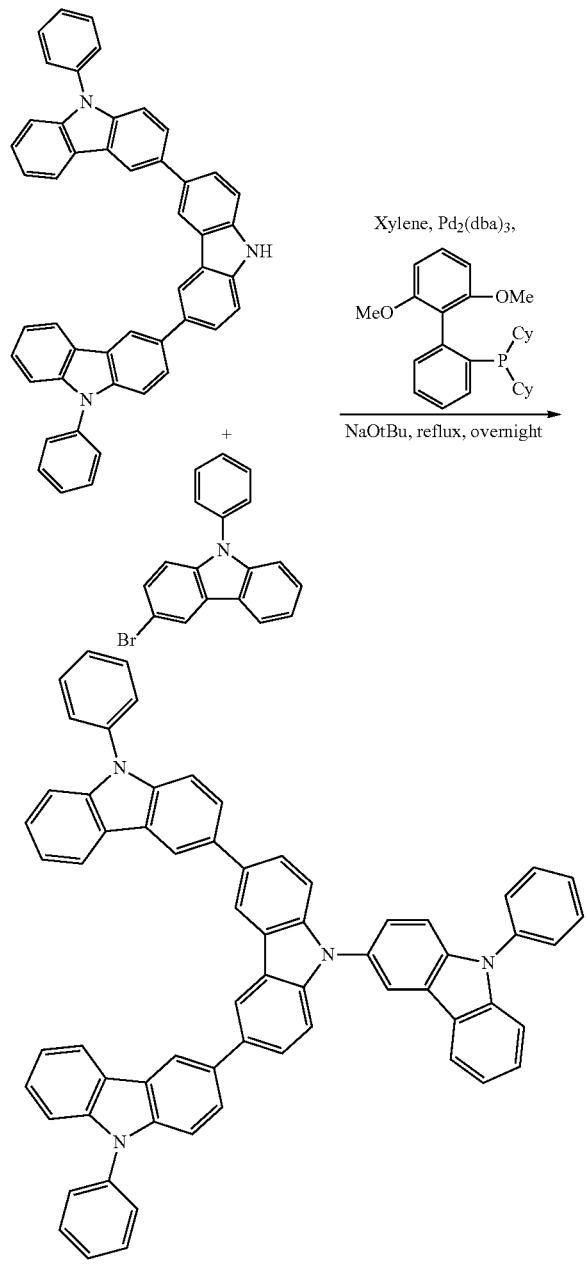

A solution of xylene (125 mL) was bubbled with nitrogen for 15 minutes 2-dicyclohexylphosphino-2',6'-dimethoxybiphenyl (1.1 g, 2.7 mmol) and $Pd_2(dba)_3$ (0.6 g, 0.7 mmol) were added. The mixture was bubbled for 15 min. 3,6-bis(9-phenylcarbazol-3-yl)carbazole, 3-bromo-9-phenylcarbazole (1.0 g, 3.1 mmol), sodium tert-butoxide (0.6 g, 6.3 mmol) were added. The mixture was bubbled for 15 min. and refluxed for 15 h. After cooling, the reaction mixture was filtered through a silica pad and washed with 80% $CH_2Cl_2$/hexane. The solvent was removed in vacuo and the residue was purified by flash chromatography using 30-40% $CH_2Cl_2$/hexane to afford Compound 5 (2.3 g, 76% yield) as a white solid.

Synthesis of Compound 7

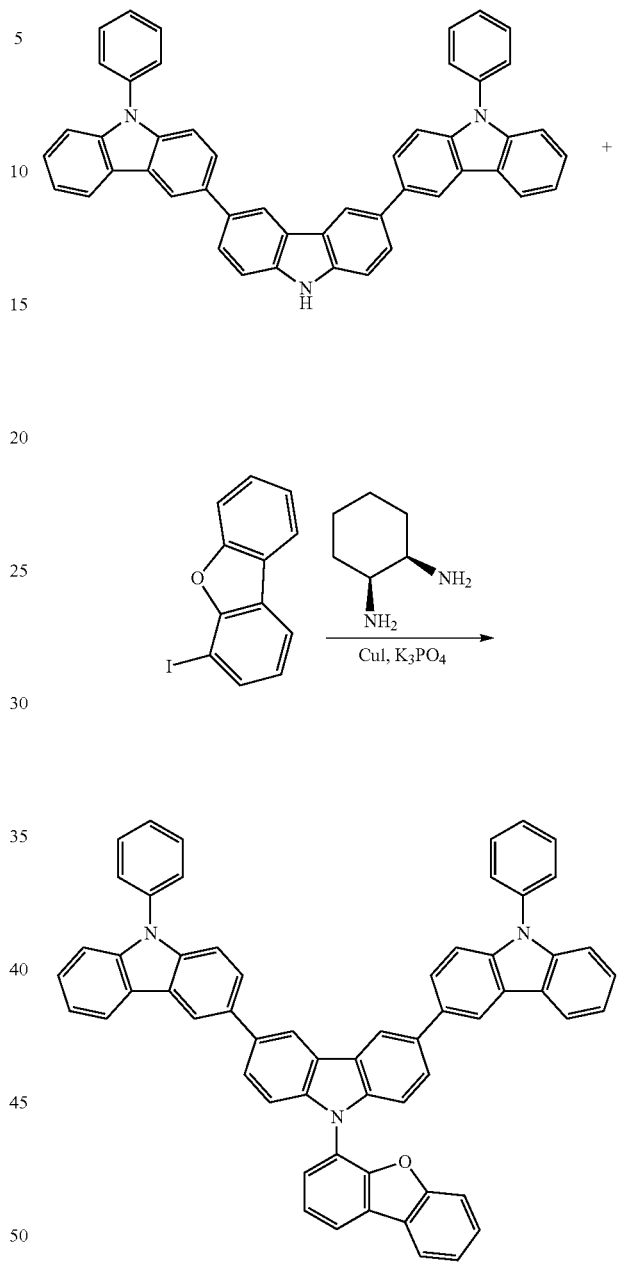

A solution of 3,6-bis(9-phenylcarbazol-3-yl)carbazole (3.61 g, 5.56 mmol) and 4-iododibenzo[b,d]furan (1.797 g, 6.11 mmol), copper(I) iodide (0.106 g, 0.556 mmol), potassium phosphate (3.54 g, 16.67 mmol) and cyclohexane-1,2-diamine (0.127 g, 1.11 mmol) in dry xylene (150 mL) was degassed and heated to reflux under $N_2$ for 48 hours. After cooling, the mixture was filtered and the filtrate was concentrated and purified by column chromatography on silica gel (hexane:DCM 1:1) to provided Compound 7 as a white solid (2.8 g, 62%).

Synthesis of Compound 9

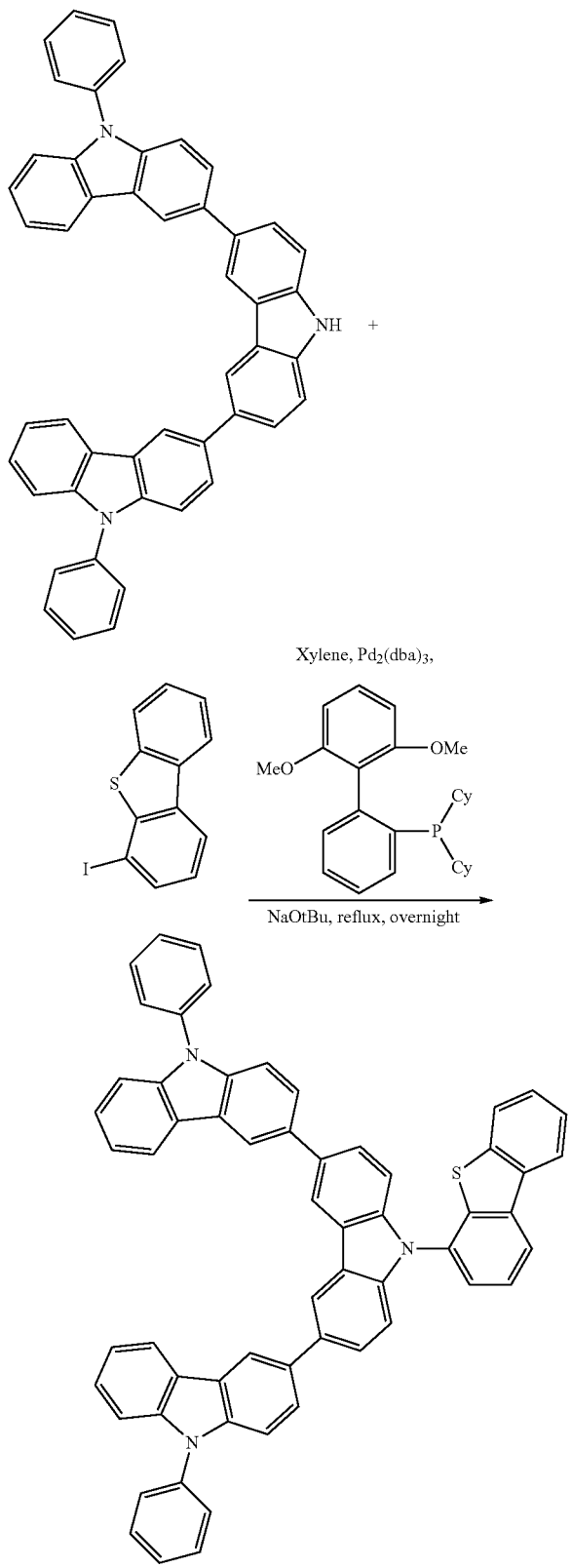

A solution of xylene (125 mL) was bubbled with nitrogen for 15 minutes, then. 2-dicyclohexylphosphino-2',6'- dimethoxybiphenyl (1.5 g, 3.6 mmol) and Pd$_2$(dba)$_3$ (0.8 g, 0.9 mmol) were added. The mixture was bubbled for 15 min, then 3,6-bis(9-phenylcarbazol-3-yl)carbazole (3.1 g, 4.8 mmol), 4-iododibenzo[b,d]thiophene (1.7 g, 5.5 mmol), and sodium tert-butoxide (0.9 g, 9.4 mmol) were added. The mixture was bubbled with nitrogen for 15 minutes and refluxed for 12 hours. After cooling, the reaction mixture was filtered through a silica pad and washed with 80% CH$_2$Cl$_2$/hexane. The solvent was removed in vacuo and the residue was purified by flash chromatography using 30-50% CH$_2$Cl$_2$/hexane to afford Compound 9 (2.5 g, 63% yield) as a white solid.

Synthesis of Compound 13

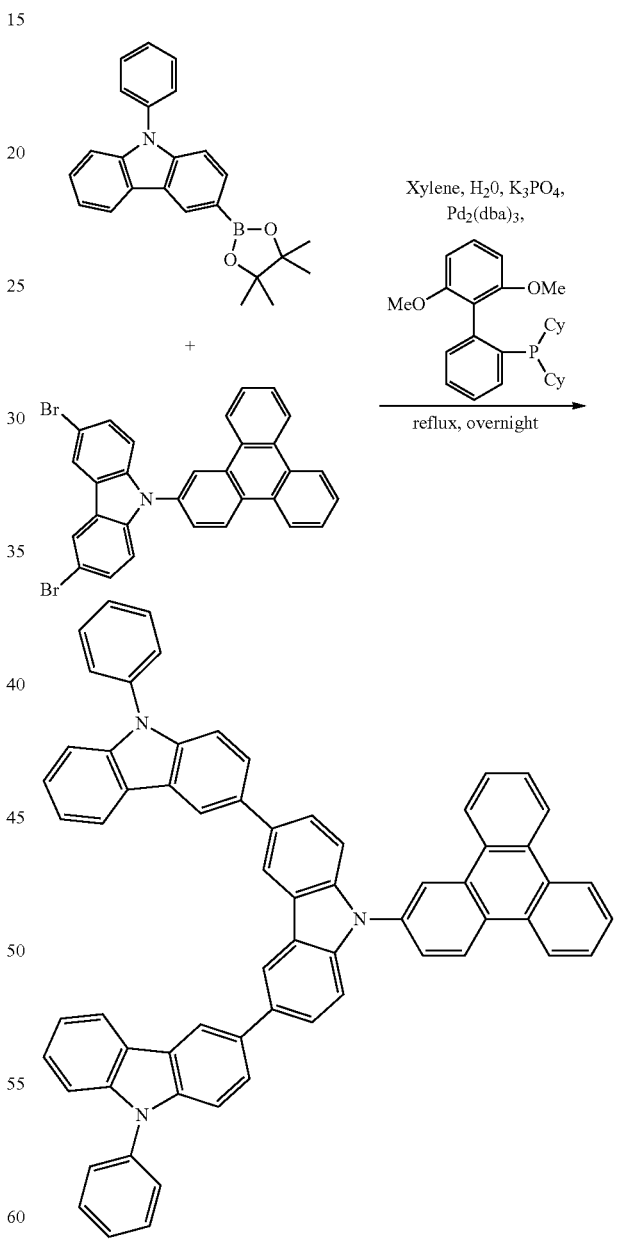

A solution of 9-phenyl-3-(4,4,5,5-tetramethyl-1,3,2-dioxaborolan-2-yl)-9H-carbazole (4.3 g, 11.7 mmol), 3,6-dibromo-9-(triphenylen-2-yl)-9H-carbazole (2.9 g, 5.3 mmol), K$_3$PO$_4$ (6.6 g, 31.1 mmol) in toluene (100 mL) and water (10 mL) was bubbled with nitrogen for 15 minutes. Then, 2-dicyclohexylphosphino-2',6'-dimethoxybiphenyl (0.4 g, 1.0 mmol) and Pd$_2$(dba)$_3$ (0.2 g, 0.2 mmol) were added. The mixture was bubbled with nitrogen for 15 minutes and refluxed for 12 hours. Bromobenzene (1.0 mL, 9.5 mmol) and Pd(PPh$_3$)$_4$ (0.3 g, 0.3 mmol) were added. The resultant mixture was refluxed for 12 hours. After cooling, the reaction mixture was filtered through a short column packed with silica and MgSO$_4$ and washed with 80% CH$_2$Cl$_2$/hexane. The solvent was removed in vacuo and the residue was purified by flash chromatography using 45% CH$_2$Cl$_2$/hexane to afford Compound 13 (3.7 g, 80% yield) as a white solid.

Synthesis of Compound 14 phenylcarbazol-3-yl)carbazole (2.7 g, 4.2 mmol), 9-(4-bromophenyl)-9H-carbazole (2.4 g, 7.5 mmol), NaO$^t$Bu (1.0 g, 10.4 mmol) were added. The mixture was bubbled for 15 min. and refluxed for 10 h. After cooling, the reaction mixture was filtered through a silica pad and washed with 75% CH$_2$Cl$_2$/hexane. The solvent was removed in vacuo and the residue was purified by flash chromatography using 30-40% CH$_2$Cl$_2$/hexane to afford Compound 14 (3.4 g, 92% yield) as a white solid.

Synthesis of Compound 15

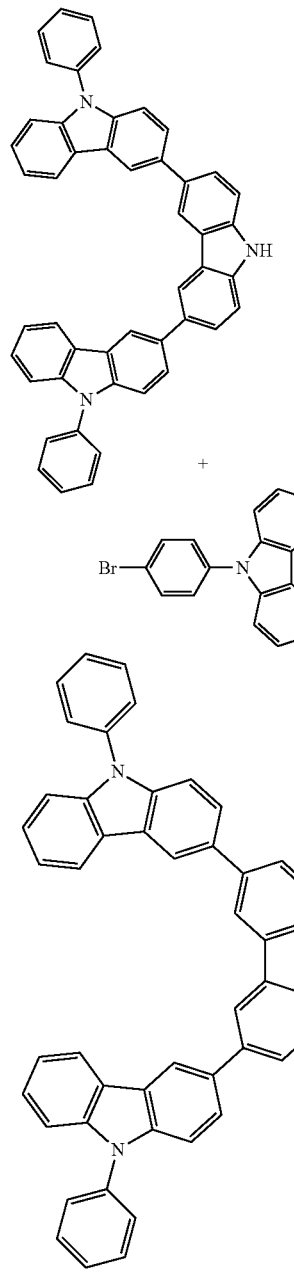

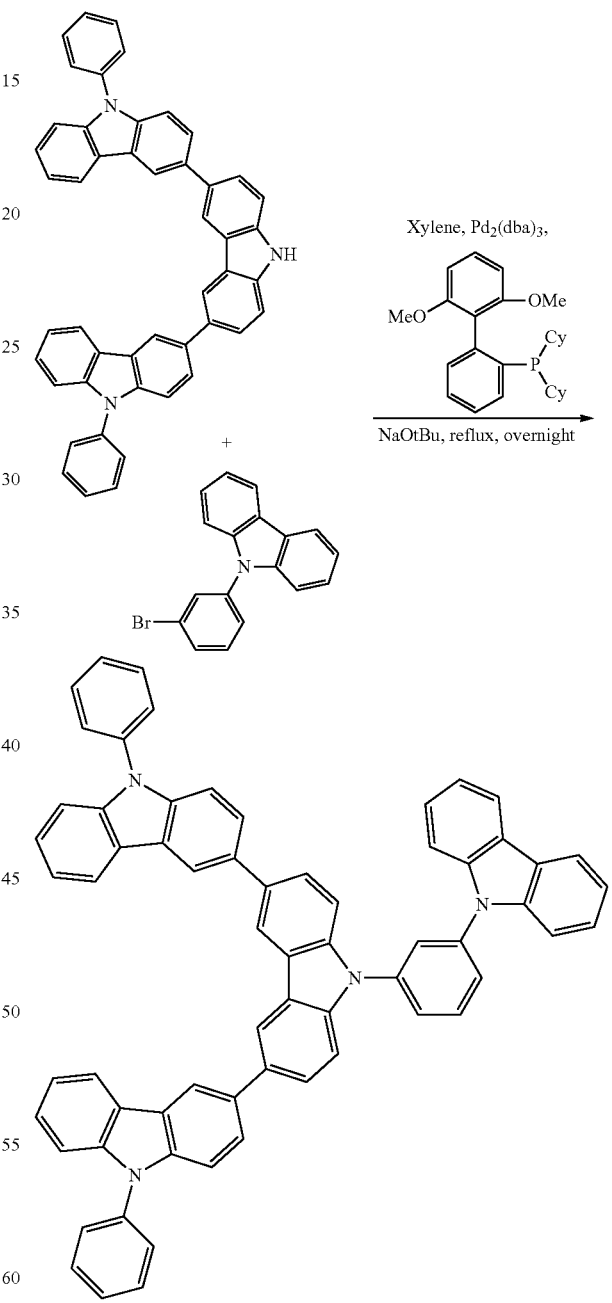

A solution of xylene (125 mL) was bubbled with nitrogen for 15 min, then 2-dicyclohexylphosphino-2',6'-dimethoxybiphenyl (0.8 g, 2.0 mmol) and Pd$_2$(dba)$_3$ (0.4 g, 0.5 mmol) were added. The mixture was bubbled for 15 min. 3,6-bis(9-

A solution of xylene (125 mL) was bubbled with nitrogen for 15 min, then 2-dicyclohexylphosphino-2',6'-dimethoxybiphenyl (0.7 g, 1.7 mmol) and Pd$_2$(dba)$_3$ (0.4 g, 0.5 mmol) were added. The mixture was bubbled with nitrogen for 15 minutes, then 3,6-bis(9-phenylcarbazol-3-yl)carbazole (2.8 g, 4.3 mmol), 9-(3-bromophenyl)-9H-carbazole (2.6 g, 8.0 mmol), and sodium tert-butoxide (0.8 g, 8.3 mmol) were added. The mixture was bubbled with nitrogen for 15 minutes and refluxed for 12 hours. After cooling, the reaction mixture was filtered through a silica pad and washed with 90% $CH_2Cl_2$/hexane. The solvent was removed in vacuo and the residue was purified by flash chromatography using 30-50% $CH_2Cl_2$/hexane to afford Compound 15 (3.6 g, 94% yield) as a white solid.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound having the formula:

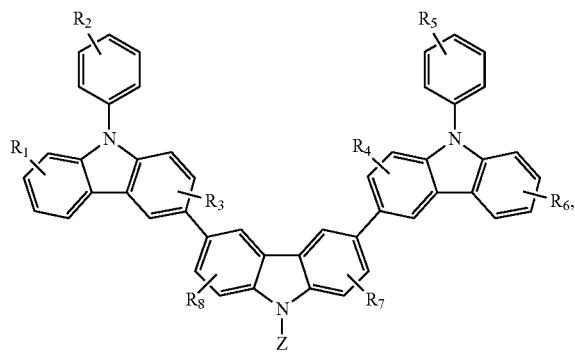

Formula I;
wherein Z is selected from the group consisting of:

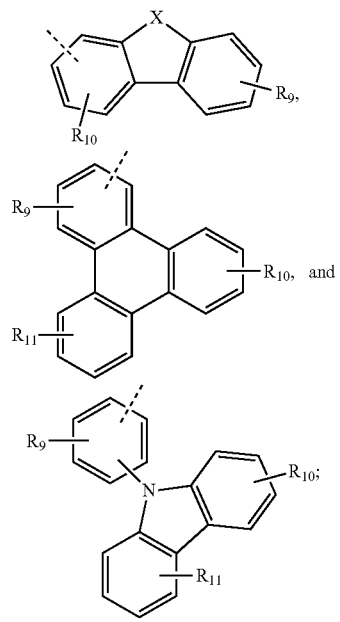

wherein X is selected from the group consisting of NR, O, S, and Se;

wherein $R_1$ to $R_{11}$ independently represent mono, di, tri, tetra substitution, or no substitution;

wherein R and $R_1$ to $R_{11}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

2. The compound of claim 1, wherein $R_1$ to $R_{11}$ represent no substitution.

3. The compound of claim 1, wherein $R_1$ to $R_{11}$ are independently aryl or heteroaryl.

4. The compound of claim 1, wherein the compound has the formula:

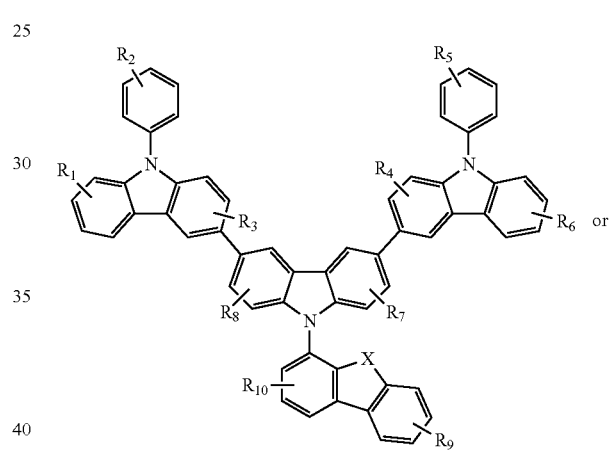

or

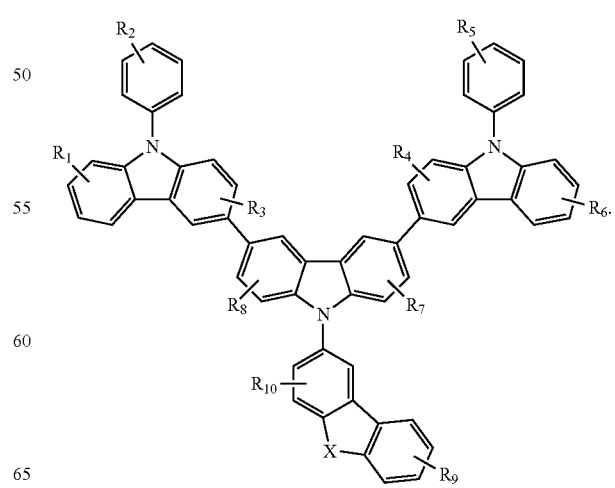

5. The compound of claim 1, wherein the compound has the formula:

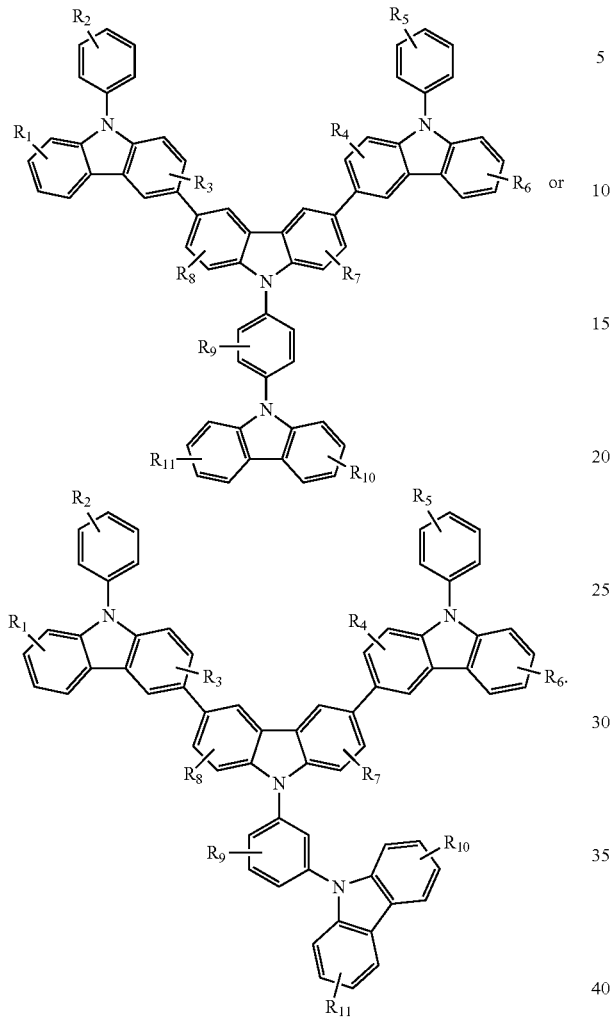

6. The compound of claim 1, wherein the compound has the formula:

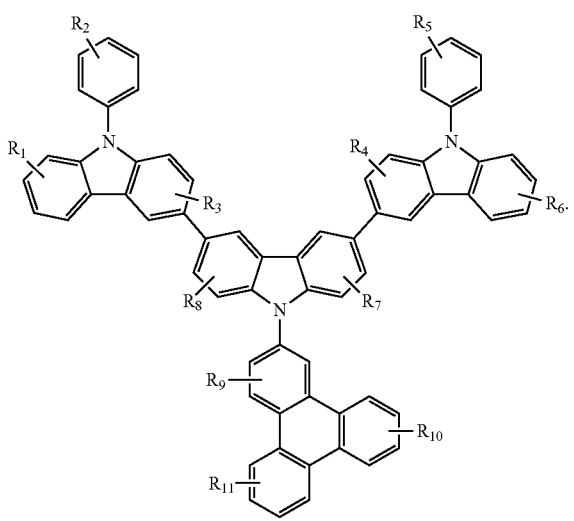

7. The compound of claim 1, wherein X is O or S.

8. The compound of claim 1, wherein $R_2$ and $R_5$ represent no substitution.

9. The compound of claim 1, wherein R is selected from the group consisting of alkyl, heteroalkyl, aralkyl, aryl and heteroaryl.

10. The compound of claim 1, wherein the compound is selected from the group consisting of:

Compound 5

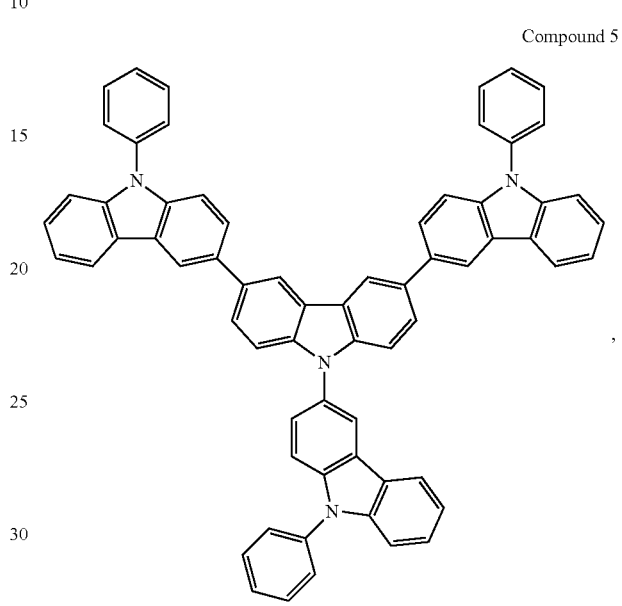

Compound 6

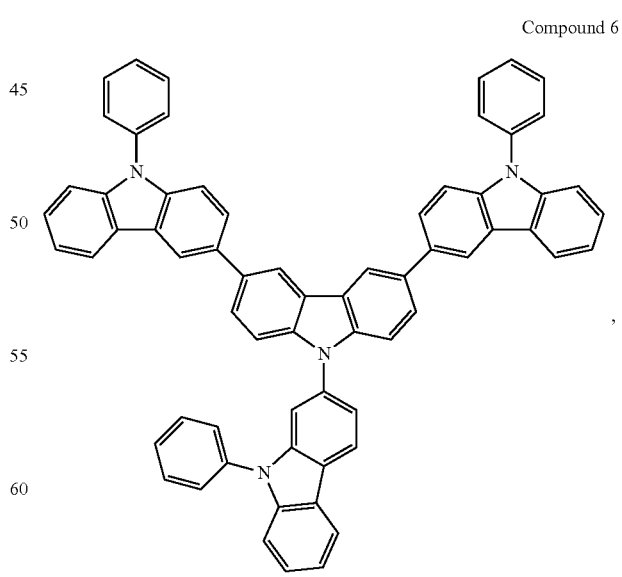

Compound 7
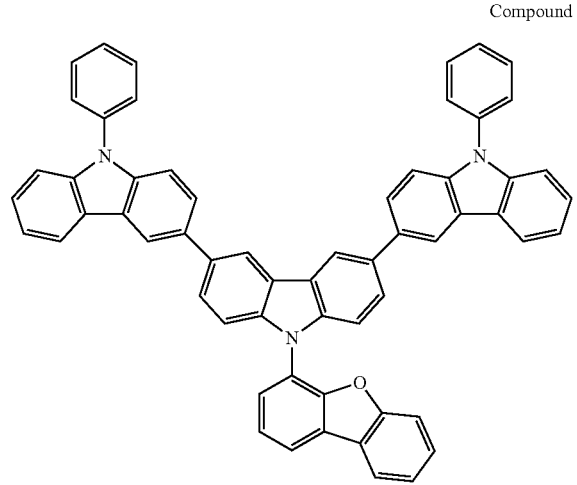
Compound 8
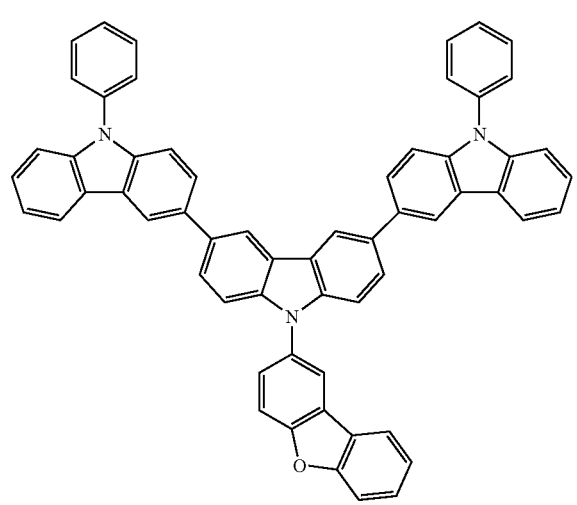
Compound 9
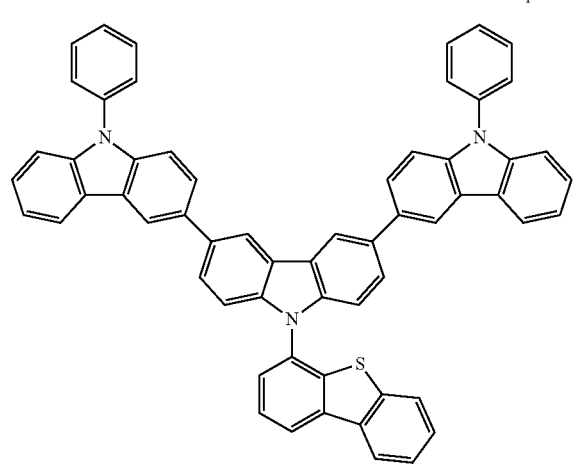
Compound 10
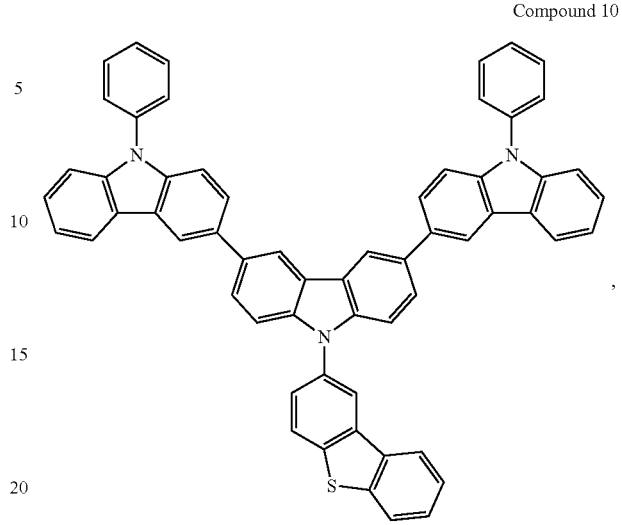
Compound 11
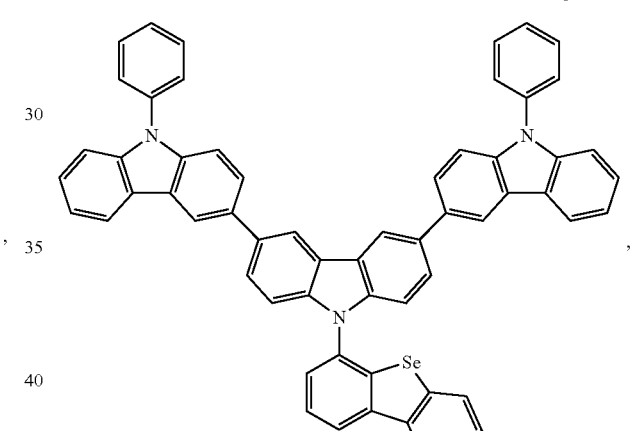
Compound 12
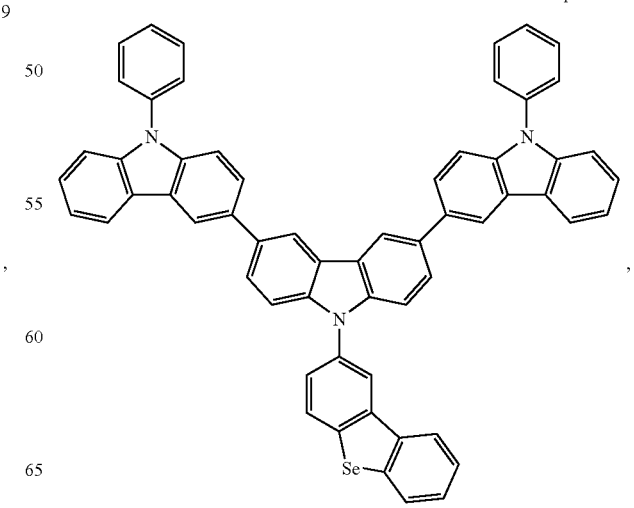

-continued

Compound 13

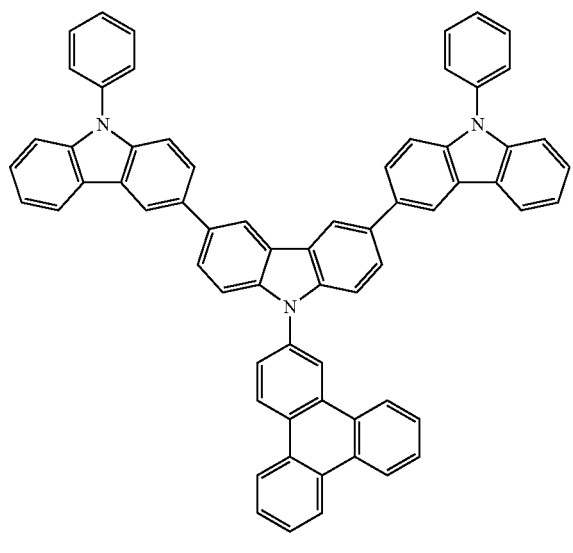

Compound 14

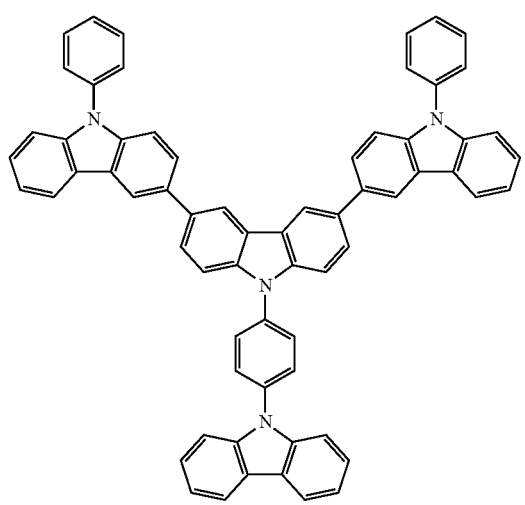
, and

Compound 15

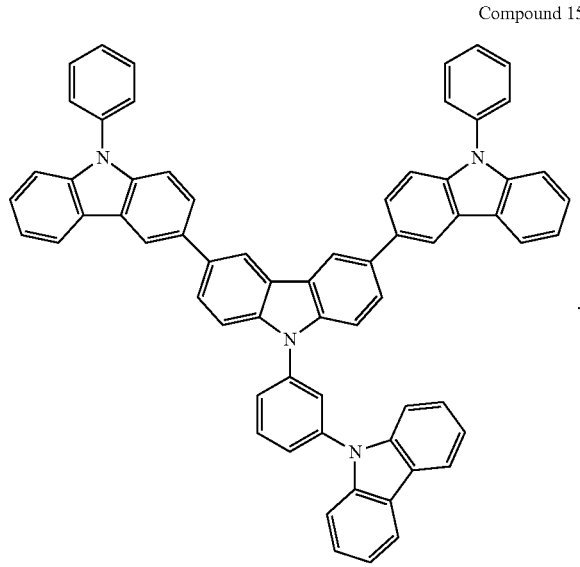

11. A first device comprising a first organic light emitting device, further comprising:
   an anode;
   a cathode;
   a hole injection layer disposed between the anode and the emissive layer;
   a first hole transport layer disposed between the hole injection layer and the emissive layer; and
   a second hole transport layer disposed between the first hole transport layer and the emissive layer;
   wherein the second hole transport layer comprises a compound of formula:

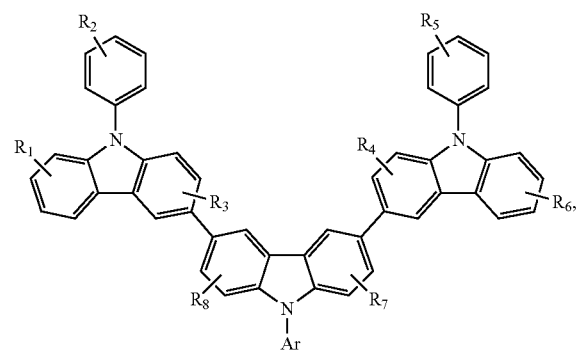

Formula II;

wherein Ar comprises aryl or heteroaryl;
wherein $R_1$ to $R_8$ independently represent mono, di, tri, tetra substitution, or no substitution; and
wherein $R_1$ to $R_8$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

12. The first device of claim 11, wherein the second hole transport layer is disposed adjacent to the first hole transport layer.

13. The first device of claim 11, wherein the first hole transport layer is thicker than the second hole transport layer.

14. The first device of claim 11, wherein Ar is selected from the group consisting of:

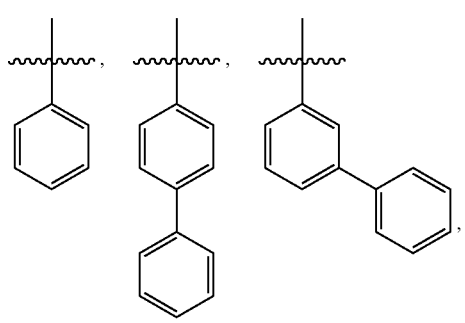

-continued

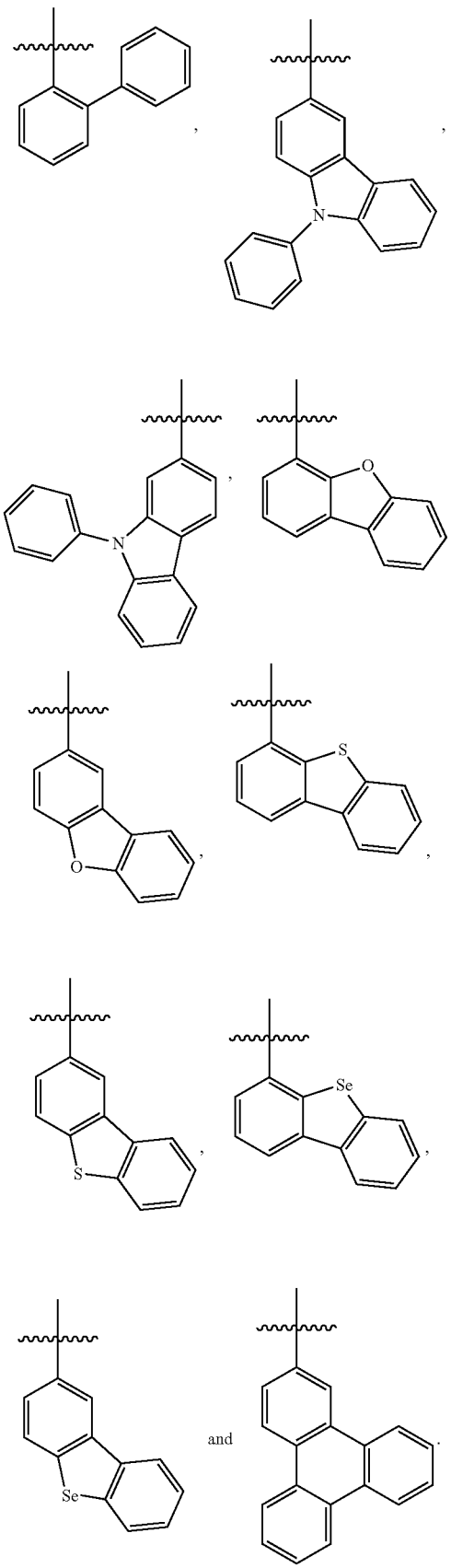

15. The first device of claim 11, wherein the compound has the formula:

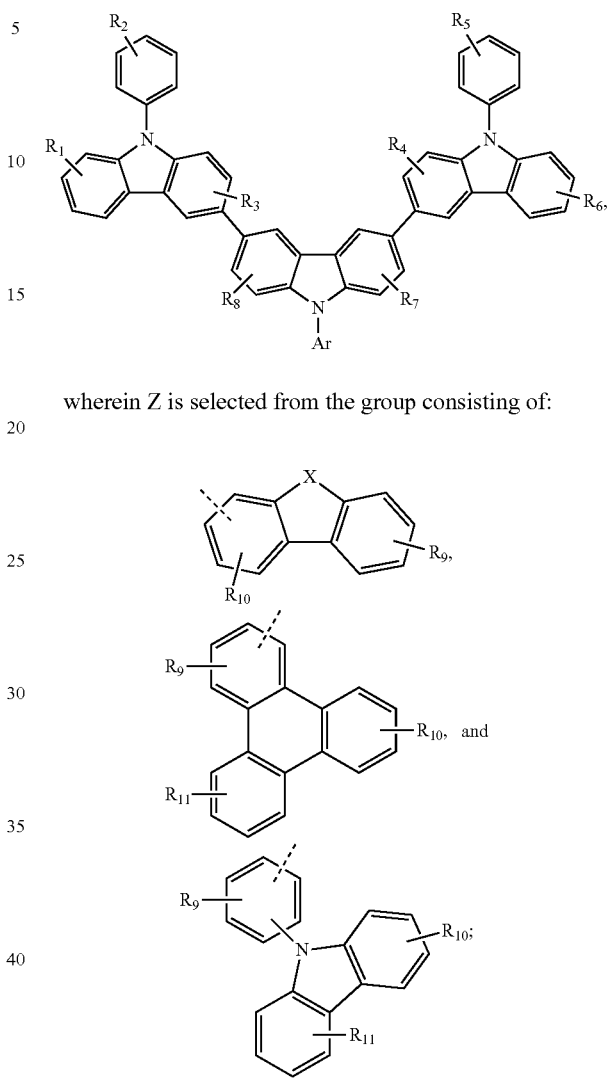

wherein Z is selected from the group consisting of:

wherein X is selected from the group consisting of NR, O, S, and Se;
wherein $R_9$, $R_{10}$, and $R_{11}$ independently represent mono, di, tri, tetra substitution, or no substitution; and
wherein R, $R_9$, $R_{10}$, and $R_{11}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

16. The first device of claim 11, wherein the first hole transport layer comprises a compound with the formula:

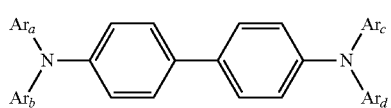

wherein $Ar_a$, $Ar_b$, $Ar_c$ and $Ar_d$ are independently selected from the group consisting of aryl and heteroaryl.

17. The first device of claim 11, wherein the triplet energy of the compound of Formula II is higher than the emission energy of the emissive layer.

18. The first device of claim 11, further comprising an emissive dopant comprising a transition metal complex having at least one ligand or part of the ligand if the ligand is more than bidentate selected from the group consisting of:

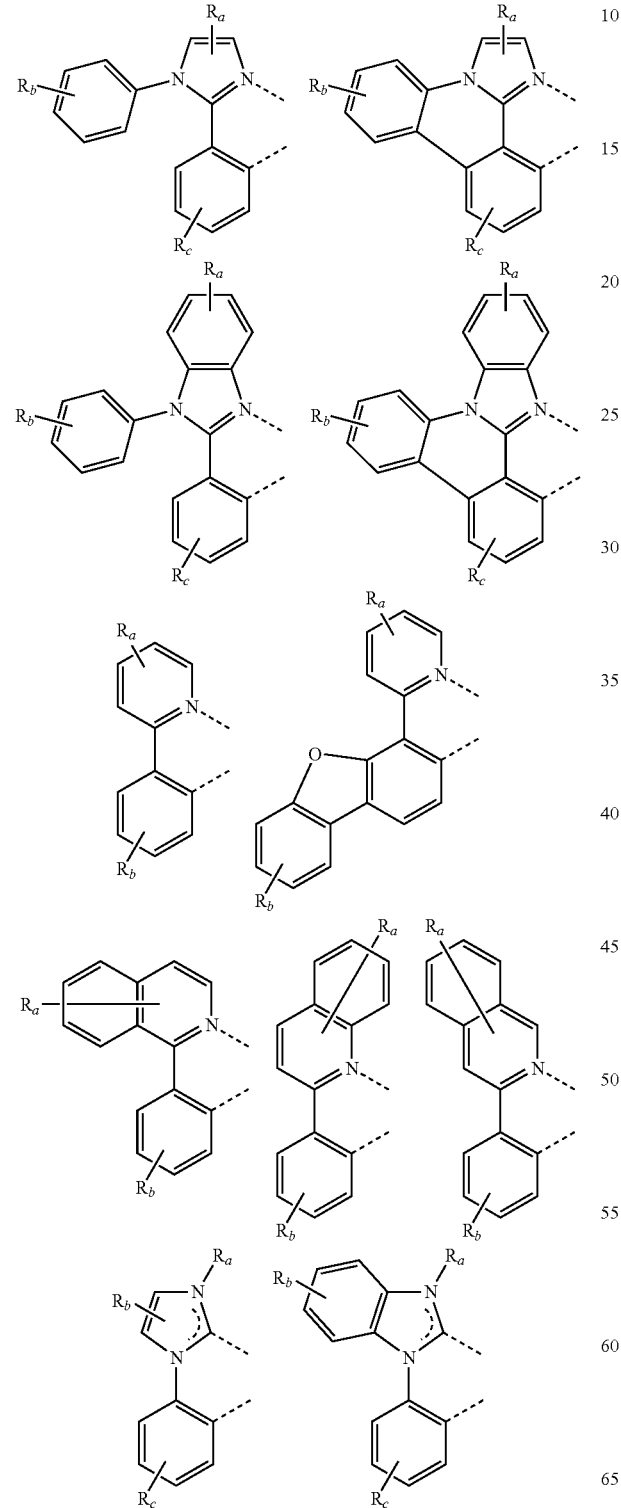
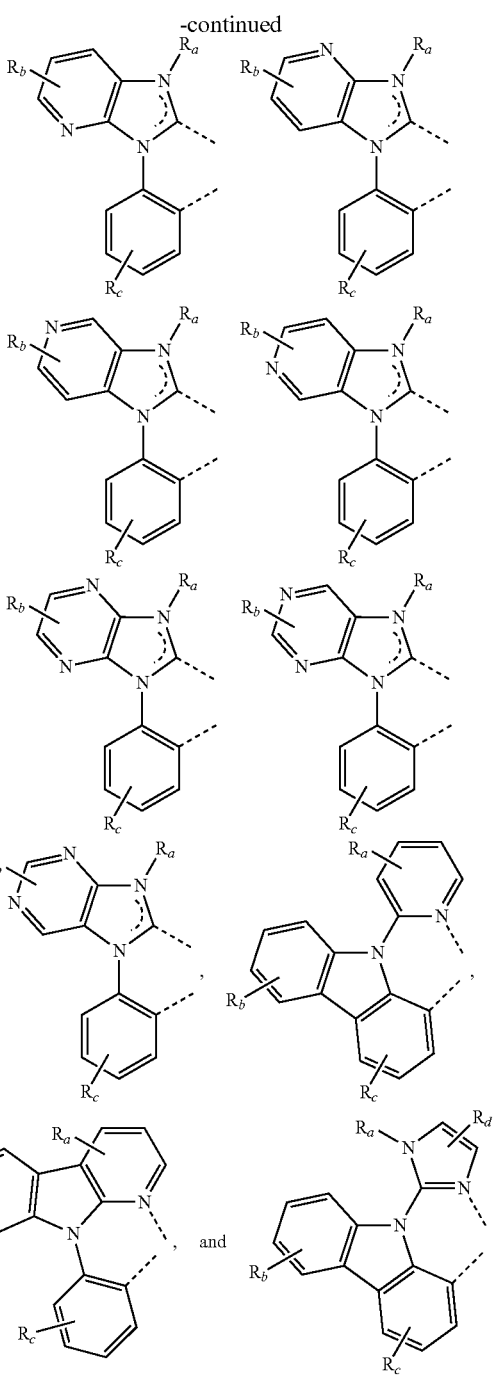

wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

19. The first device of claim 11, wherein the first device is a consumer product.

20. The first device of claim 11, wherein the first device is an organic light-emitting device.

21. The first device of claim 11, wherein the first device comprises a lighting panel.

22. A first device comprising an organic light emitting device, further comprising:
an anode;
a cathode;
a first organic layer disposed between the anode and the cathode; and
wherein the first organic layer comprises a compound of formula:

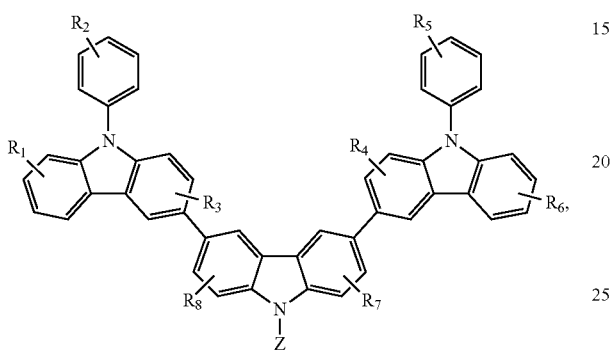

Formula I;
wherein Z is selected from the group consisting of:

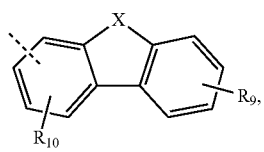

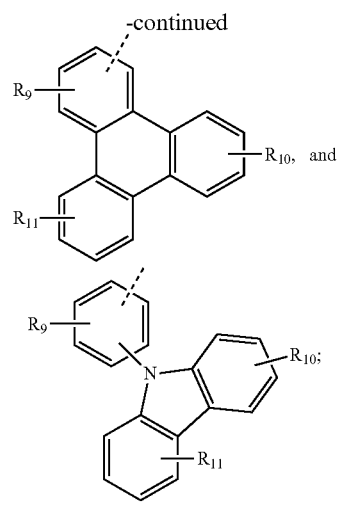

wherein X is selected from the group consisting of NR, O, S, and Se;

wherein $R_1$ to $R_{11}$ independently represent mono, di, tri, tetra substitution, or no substitution; and wherein R, and $R_1$ to $R_{11}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

23. The first device of claim 22, wherein the first organic layer is an emissive layer.

24. The first device of claim 23, wherein the emissive layer is a phosphorescent emissive layer.

* * * * *